United States Patent [19]

Nishihashi et al.

[11] Patent Number: 4,590,160
[45] Date of Patent: May 20, 1986

[54] PROCESS FOR PRODUCTION OF β-GLYCOSYL STEVIOSIDE DERIVATIVES

[75] Inventors: Hideji Nishihashi, Urawa; Tadao Matsubayashi, Chiba; Tadashi Katabami, Urawa; Ken-ichi Matsuda, Tokyo, all of Japan

[73] Assignees: Dainippon Ink and Chemicals, Inc.; Dic Fine Chemicals, Inc., both of Tokyo, Japan

[21] Appl. No.: 469,947

[22] Filed: Feb. 25, 1983

[30] Foreign Application Priority Data

Feb. 27, 1982 [JP] Japan ................................. 57/31479

[51] Int. Cl.[4] ...................... C12P 19/56; C12P 19/18; A23L 1/236
[52] U.S. Cl. ...................................... 435/78; 435/97; 426/52; 426/548; 426/804; 514/974
[58] Field of Search ...................... 424/48, 58; 426/48, 426/52, 548, 658, 648, 804; 435/72, 78, 96, 97, 99; 514/974

[56] References Cited

U.S. PATENT DOCUMENTS 4,219,571  8/1980  Miyake ................................. 435/48

OTHER PUBLICATIONS

Kaneda et al., Chemical Studies on Sweet Diterpene—Glycosides of *Stevia rebaudiana* . . . , 1977, Chem. Pharm. Bull., 25(9), 2466–2467.
Enzyme Nomenclature, 1978 (Academic Press, 1979), pp. 160–185.
Brown, in "Handbook of Microbiology" (CRC 1973), vol. 3, pp. 633–635.
Kameda et al., Microbial Glycosidation of Validamycin II . . . , Jul. 1980, J. of Antibiotics, vol. 33 (7), pp. 764–766.

*Primary Examiner*—Thomas G. Wiseman
*Assistant Examiner*—Elizabeth C. Weimar
*Attorney, Agent, or Firm*—Sherman & Shalloway

[57] ABSTRACT

A process for producing a stevioside derivative, which comprises reacting stevioside with a β-1,3- or β-1,4-glycosyl sugar compound in aqueous solution or aqueous suspension in the presence of a microorganism or enzyme having β-1,3- or β1,4-glycosyl transferring activity thereby to form β-1,3- or β-1,4-glycosyl stevioside.

20 Claims, 8 Drawing Figures

PROCESS FOR PRODUCTION OF β-GLYCOSYL STEVIOSIDE DERIVATIVES

BACKGROUND OF THE INVENTION

This invention relates to a process for producing β-stevioside derivatives. More specifically, this invention relates to a process for producing β-1,3 or β-1,4-glycosyl stevioside which comprises reacting stevioside with a β-1,3- or β-1,4-glycosyl sugar compound in aqueous solution or suspension (to be referred to inclusively as aqueous solution) in the presence of β-1,3- or β-1,4-glycosyltransferase or a microorganism having β-1,3- or β-1,4-glycosyl transferring activity. According to an especially preferred embodiment, this invention pertains to a process for producing stevioside derivatives intended for the production of rebaudioside A by a fermentation technique.

In recent years, the use of such artificial sweeteners as sodium cyclamate, sodium saccharin and dulcin, in food has been prohibited or restricted from the standpoint of safety, and on the other hand, an adverse effect of the excessive intake of sugar on health has become a problem. It has been eagerly desired therefore to develop natural sweeteners which would replace these artificial ones. Under the circumstances, a demand for stevioside has rapidly increased because unlike sugar, it is a sweetener of a low caloric value and has a sweetness ratio about 300 times as high as that of sugar. Stevioside is a sweetening component (contained in an amount of 6 to 12%) extracted from *Stevia rebaudiana* BERTONI (to be referred to simply as Stevia) belonging to the family Compositae, and is a β-glucosyl glycoside in which the aglycon is steviol. Stevioside is now used to sweeten foods and drinks. The sweetness of stevioside appears more slowly than sugar, and remains longer as an unpleasant aftertaste. Furthermore, it also has bitterness and astringency. It is thought that because of such a defect, there is a limit to its usage and its amount used, and some improvement in the quality of its sweetness is required. Attempts are made to improve the quality of the sweetness of stevioside by adding at least one natural sweetener such as sucrose, glucose or fructose, or by adding an amino acid or its hydrochloride. According to these methods, the amounts of the aforesaid additives should be made extremely large in order to reduce the bitterness and astringency of the extract of Stevia. Subsequently, the characteristics of stevioside as a low-calorie sweetener are lost.

Rebaudioside A (β-1,3-monoglucosyl stevioside) is contained in an amount of about 2 to 6% in the leaves or stalks of Stevia, and is the second highest in content following stevioside (6 to 12%), a main ingredient. Heretofore, a mixture of these ingredients has been used as a Stevia sweetener. Stevioside has bitterness and leaves an unpleasant aftertaste, whereas rebaudioside A has mild sweetness without bitterness and has a higher sweetness ratio to sucrose than stevioside.

Recently, a Stevia sweetener having improved taste and being free from bitterness without an increase in calorie was developed by forming an α-glycosyl stevioside (U.S. Pat. No. 4,219,571). This sweetener, however, has the defect that its sweetness ratio is lower than stevioside. Since this sweetener has added thereto an α-glucosyl sugar compound unlike a β-glycosyl sugar compound in the present invention, it has "sticky" sweetness different from the sweetness of sugar. In contrast, the sweetener in accordance with this invention having a β-glycosyl sugar compound added thereto has sharp sweetness which is close to that of sugar.

Heretofore, rebaudioside A has been obtained by a method which comprises obtaining a mixture of stevioside and rebaudioside A by extraction from the dried leaves of Stevia followed by purification, removing stevioside from the mixture by crystallization, and repeatedly re-crystallizing the residue. Since the yield of the rebaudioside A is poor, it is necessary to increase the content of rebaudioside A when extracting the aforesaid mixture. An attempt has been made to obtain Stevia leaves having an increased content of rebaudioside A by breeding Stevia, but because of the instability of maintaining the character by heredity, this technique has little practical utility at present.

The present inventors, therefore, have made extensive investigations in order to convert stevioside present in the largest amount in the extract of Stevia leaves into β-glucosyl stevioside and β-galactosyl stevioside by the addition-reaction of glucose or galactose with it by a fermentation or enzyme technique.

SUMMARY OF THE INVENTION

According to the present invention, a β-glycosyl stevioside is produced by reacting stevioside with a β-1,3- or β-1,4-glucosyl sugar compound or a β-1,4-galactosyl sugar compound (for example, polysaccharides derived from microorganisms such as curdlan, pachyman and laminarin, vegetable polysaccharides such as cellulose, cellobiose, and tamarind seed extract, or partially decomposed products of these and lactose) in aqueous solution in the presence of an enzyme having the activity of transferring glucose or galactose in the sugar compound to stevioside, i.e. β-1,3- or β1,4-glucosyl or β-1,4-galactosyl sugar transferring activity, a microorganism capable of producing such an enzyme, or a cellulase preparation.

The β-glycosyl stevioside produced by such a method is believed to be one having a β-1,3- or β-1,4-glucosyl or galactosyl group at one or more of three β-glucosyl groups derived respectively from β-D-glucose bonded to the hydroxyl group of steviol (aglycon in Stevia), β-D-glucose bonded to the hydroxyl group at its $C_2$, and β-D-glucose bonded to the carboxyl group of steviol, namely β-1,3- or β-1,4-glucosyl stevioside, β-1,3- or β-1,4-diglucosyl stevioside, β-1,3- or β-1,4-triglucosyl stevioside, a mixture of these, β-1,4-galactosyl stevioside, or β-1,4-digalactosyl stevioside. The β-1,3- or β-1,4-glycosyl stevioside is also considered to be a compound resulting from the β-1,3 or β-1,4 bonding of at least one β-1,3 or β-1,4-glucane having at least two glucose units, or a mixture of these with each other or with the aforesaid β-1,3- or β-1,4-glycosyl stevioside. β-1,3-Monoglucosyl stevioside having a β-glucosyl group bonded at β-1,3 to the β-glucosyl group bonded to the hydroxyl group of steviol is rebaudioside A whose sweetness is recognized to be especially good. In the present invention, it is most preferred that the β-1,3-glycosyl stevioside is rebaudioside A.

The β-1,3-glycosyl stevioside obtained by this invention is free from bitterness of astringency and has mild sweetness because unlike conventional stevioside products or mixtures of stevioside and other sweeteners, it is rebaudioside A or has a structure similar to it. Another excellent property is that its unpleasant aftertaste does not persist for long, and its solubility increases.

DETAILED DESCRIPTION OF THE INVENTION

Figure 1:
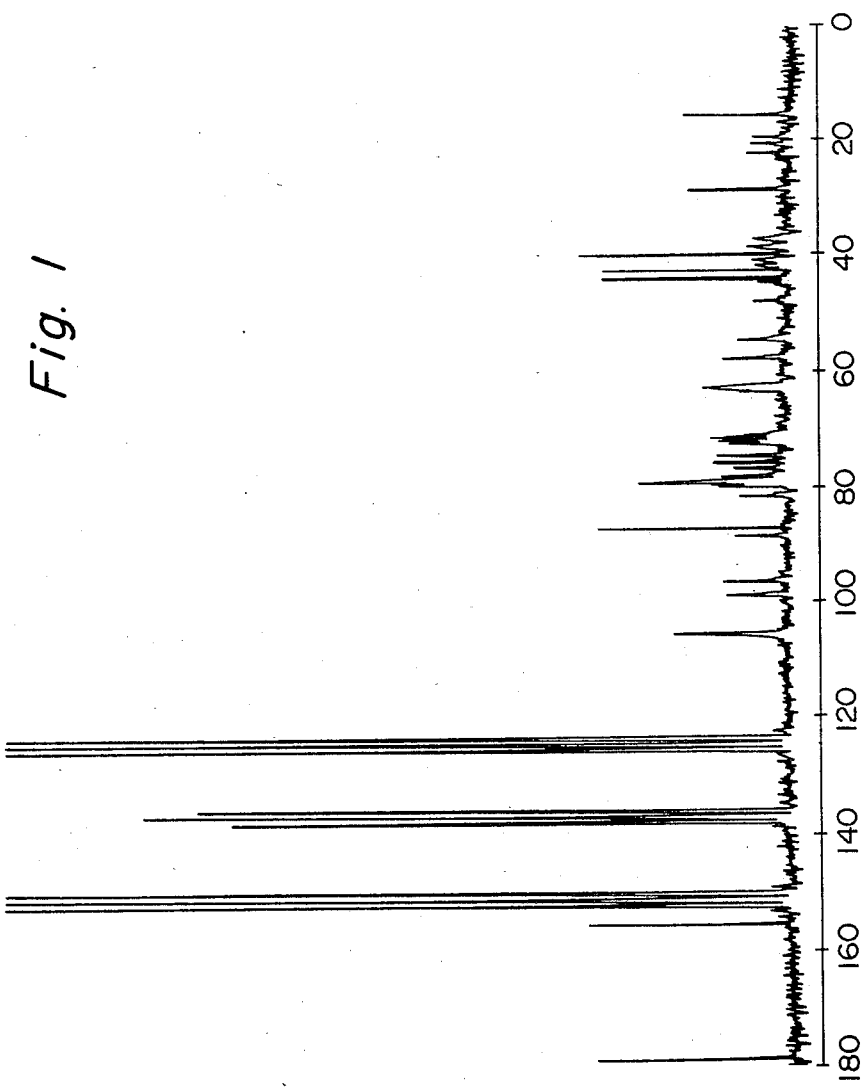
FIG. 1 is a $^{13}$C-NMR chart.

The stevioside used in this invention needs not to be limited to a highly purified stevioside, and a mixture of stevioside and rebaudioside A may be used. A crude product of stevioside containing other impurities can also be used in this invention.

The β-1,3-glucosyl sugar compound used in the process of this invention may be any sugar compound which converts rebaudioside A from stevioside by Streptomyces sp. DIC-108, Streptomyces sp. DIC-146, etc. Examples of these sugar compounds include pachyman, curdlan, laminarin, cell walls of yeasts, partially decomposed products of the yeast cell walls (the yeasts, as referred to herein, are those belonging to the genera Saccharomyces, Candida, Pichia, Schizosaccharomyces, Torulopsis, Hansenula, etc.), leucosin (cell walls of Bacillariophyceae), callose (cell walls of a higher plant, Phaseolus), paramylon (cell walls of single-celled algae), and lichenan (an extract of moss). Preferred sugar compounds are pachyman, curdlan and laminarin because for one thing they are easily available. Curdlan is a water-insoluble β-glucan having a β-1,3-glucoside linkage as a main structure, and is a generic term for a polysaccharide which forms an elastic, thermally irreversible gel when its suspension is heated. Curdlan products produced by microorganism are now commercially available. (See Agr. Biol. Chem., 29, 757, 1965, and "Hakko to Kogyo" (Fermentation and Industry), 36, 2, 1978).

Examples of β-1,4-glucosyl sugar compounds used in the present invention are cellobiose and a partial decomposition product of cellulose. Examples of β-1,4-galactosyl sugar compounds are lactose and an extract of tamarind seed.

The vegetable polysaccharides mentioned hereinabove denote polysaccharides extracted from the seeds of plants, for example those containing a β-1,4-or β-1,3-glucose, xylose or galactose and obtained from the seeds of leguminous plants such as rape, red kidney bean, soybean, cowpea and tamarind, and seeds of gramineous plants such as rice, barley and wheat, which can yield at least one such β-type monosaccharide, or at least one oligosaccharide resulting from the combination of such monosaccharides, under the action of a β-1,3- or β-1,4-transferase. Needless to say, they may contain tiny amounts of arabinose, fructose or another monosaccharide.

In particular, polysaccharides obtained from the seeds of tamarind (Tamarindus indica) are preferred, and are commercially available under the trademark "GLYLOID 3S, 3A, C-102" (a trademark for a product of Dainippon Pharmaceutical Co., Ltd.).

The enzyme or microorganism which transfers such a sugar compound to stevioside is properly selected depending upon the sugar compounds to be used. For example, when cellulose or cellobiose which is a β-1,4-glucosyl sugar compound is used, yeasts of the genus Rhodotorula such as Rhodotorula minuta IFO-1540 and Rhodotorula marina IFO-1421, enzymes obtained from these yeasts, and commercially available cellulase preparations such as CELLULASE "ONOZUKA" (trademark, Kinki Yakult Co., Ltd.), MEISELASE (trademark, Meiji Seika Co., Ltd.) and DRISELASE (trademark, Kyowa Hakko Co., Ltd.) are used. When lactose, which is a β-1,4-galactosyl sugar compound, or a vegetable polysaccharide containing it is used, yeasts of the genus Rhodotorula such as Rhodotorula minuta IFO-1540, Rhodotorula marina IFO-1421 and Rhodotorula lactosa IFO-1424, and enzymes obtained from these microorganisms are preferably used. Furthermore, when a β-1,3-glucosyl sugar compound is used, there may be used β-1,3-glucanases such as laminarinase (E.C.3.2.1.6) and ZYMOLYASE (trademark, a product of Seikagaku Kogyo Co., Ltd.) as a β-1,3-glucosyl transferase, and DRISELASE cited above as a cellulase preparation.

The microorganism used in this invention may be molds, actinomycetes, bacteria, yeasts, basidyomycetes, etc. which have β-1,3-glycosyl transferring activity. Examples include various molds belonging to the genera Trichoderma, Rhisopus, Chaetomium, Myriococcum, Thermomyces, Aspergillus, Penicillium, Myrothecium, Mucor, Sporotrichum, Sclerotinia, Rhizoctonia, Sclerotium, and Pellicularia; various actinomycetes belonging to the genera Streptomyces Micropolyspora and Oerskovia; various bacteria belonging to the genera Bacillus, Brevibacterium, Arthrobacter and Flavobacterium; yeasts of the genus Schizosaccharomyces; and various basidyomycetes belonging to the genera Trametes, Irpex and Coprinus. Especially, microorganisms belonging to the genera Bacillus, Irpex, and Arthrobacter are of good glycosyl transferring activity. Examples of microorganisms that can be used in this invention are tabulated below.

| Microorganism | | β-1,3-glucosyl transferring activity |
|---|---|---|
| Trichoderma viride | ATCC 26921 | + |
| Rhizopus arrhizus | ATCC 24563 | ++ |
| Chaetomium thermophilum | IFO 30072 | + |
| Myriococcum albomyces | ATCC 16425 | + |
| Thermomyces lanuginosus | IFO 9738 | + |
| Thermomyces ibadaensis | ATCC 22716 | + |
| Penicillium funiculosum | IFO 6345 | + |
| Penicillium lilacinum | IFO 5350 | + |
| Myrothecium verrucaria | IFO 6113 | ++ |
| Myrothecium roridum | IFO 9531 | ++ |
| Mucor pusillus | ATCC 24923 | + |
| Aspergillus oryzae | ATCC 11488 | + |
| Sporotrichum pruinosum (Chrysosporinum) | ATCC 24782 | ++ |
| Sclerotinia libertiana | ATCC 20025 | + |

-continued

| Microorganism | | β-1,3-glucosyl transferring activity |
|---|---|---|
| Rhizoctonia solani | IFO 30464 | + |
| Sclerotium rolfsii | ATCC 24459 | + |
| Pellicularia filamentosa f. sp. sasakii | ATCC 20365 | ++ |
| Micropolyspora sp. | ATCC 21489 | + |
| Oerskovia turbata | ATCC 25835 | ++ |
| Bacillus circulans | ATCC 21367 | +++ |
| Bacillus coagulans | ATCC 21366 | +++ |
| Brebibacterium liticum | ATCC 15921 | + |
| Arthrobacter luteus | ATCC 21606 | +++ |
| Flavobacterium sp. | ATCC 21044 | ++ |
| Schizosaccharomyces pombe | ATCC 26192 | + |
| Trametes sanugineus | ATCC 14622 | ++ |
| Irpex lacteus | ATCC 20157 | +++ |
| Coprinus macrovhizus i. microsporus | ATCC 20120 | + |

The reaction of converting stevioside by the microorganisms exemplified above give two or more β-1,3 glucosyl steviosides containing rebaudioside A, but the molar conversion to rebaudioside A is less than 20%. Hence, the present inventors separated many microorganisms from the soil in nature in order to select microorganisms which have the ability to convert stevioside to rebaudioside A in high conversions and with marked specificity. Consequently, they have found microorganisms of the genus Streptomyces which have strong β-1,3-glucosyl transferring activity and have the ability to convert stevioside only to rebaudioside A at a high molar conversion.

The microorganisms of the genus Streptomyces used in this invention may be any microorganisms which contain β-1,3-glucosyl transferase and convert rebaudioside A from stevioside and β-1,3-glucosyl sugar compounds. Preferred microorganisms are Streptomyces sp. DIC-108 and Streptomyces sp. DIC-146 described below. Other preferred microorganisms are natural mutants of these strains, or artificial mutants of these strains obtained by artificial mutation treatments by chemical or physical means.

The two strains preferably used in this invention have the following microbiological properties.

[Microbiological properties of Streptomyces sp. DIC-108]

(1) Morphological characteristics

Good growth on used media (including an ISP medium). Abundant aerial mycelia formed on salt-starch agar, oatmeal agar and yeast-malt agar. Spore chains are spiral or retinaculiaperti. Spores are usually 0.7 to 0.8 μm wide and 1.0 to 1.2 μm long. Spores are oval and their surface is warty in a scanning electron microphotograph.

(2) Cultural characteristics on various media (1) Sucrose-nitrate agar (37° C.)

Substrate mycelium olive or pale yellowish brown; no aerial mycelium; no soluble pigment.

(2) Glucose-asparagine agar (37° C.)

Substrate mycelium pale yellowish white; no aerial mycelium; no soluble pigment.

(3) Glycerol-asparagine agar (ISP medium No. 5, 37° C.)

Substrate mycelium pale yellow; no aerial mycelium; no soluble pigment.

(4) Starch agar (ISP medium, 37° C.)

Substrate mycelium colorless; greenish gray aerial mycelium; no soluble pigment.

(5) Tyrosine agar (ISP medium-7, 37° C.)

Substrate mycelium olive or pale yellowish brown; on the 7th day of cultivation, no aerial mycelium formed, but on the 14th day, grayish white aerial mycelium formed; no soluble pigment.

(6) Nutrient agar (37° C.)

Substrate mycelium greenish grayish dark brown; pale greenish gray aerial mycelium; no soluble pigment.

(7) Yeast-malt extract agar (ISP medium-2, 37° C.)

Substrate mycelium olive or pale yellowish brown; pale greenish gray aerial mycelium; no soluble pigment.

(8) Oatmeal agar (ISP medium-3, 37° C.)

Substrate mycelium colorless; greenish brownish gray aerial mycelium; no soluble pigment.

(3) Physiological properties (1) Growth temperature range

Grows at 30° to 50° C. in a growth test on a yeast extract-malt extract liquid medium, bu the optimum growth temperature is 37° to 45° C.

(2) Liquefaction of gelatin: negative (3) Coagulation and peptonization of skimmed milk: negative (4) Formation of melanine pigment (peptoneyeast-iron agar medium, ISP medium 6): negative (5) Hydrolysis of starch: positive (a white ring formed in the hydrolysis zone)

(6) Utilization of carbon sources (Pridham-Gotlieb agar medium-9, 37° C.)

Grows by well utilizing D-glucose, L-arabinose, D-xylose, D-fructose, inositol, L-rhamnose, D-mannitol and galactose. Does not utilize sucrose, raffinose and salicin.

(7) Composition of the cell wall

Belongs to Type I in accordance with the sugar composition types described in ISP.

From the above characteristics, the present strain is determined to belong to the genus Streptomyces. The color of its aerial mycelia leads to the determination that it is included in gray series and belongs to a non-chromogenic strain which does not form a melanine pigment.

Known strains have been investigated for the taxonomical status of the present strain on the basis of the foregoing characteristics. *Streptomyces aravicus* (International Journal of Systematic Bacteriology, Vol. 18, No. 2, page 294, 1968), *Streptomyces griseoflavus* (International Journal of Systematic Bacteriology, Vol. 19, No. 4, page 433, 1969), *Streptomyces macrosporeus* (International Journal of Systematic Bacteriology, Vol. 18, No. 2, page 142, 1968), and *Streptomyces matensis* (International Journal of Systematic Bacteriology, Vol. 18, No. 2, page 344, 1968) can thus be cited as strains analogous to DIC-108. *Streptomyces aravicus* IFO-14035, *Streptomyces griseoflavus* IFO-12372, *Streptomyces macroporeus* IFO-12794 and *Streptomyces matensis* IFO-12889 which are deposited in Institute of Fermentation, Osaka, Japan have been cultivated under the same conditions, and compared with the present strain. *Streptomyces aravicus* and *Streptomyces griseoflavus* evidently differ from the present strain in that they do not hydrolyze starch. Both *Streptomyces macrosporeus* and *Streptomyces matensis* hydrolyze starch, but only *Streptomyces matensis* forms a white ring in the hydrolysis zone, which is inherent to the present strain. *Streptomyces*

*matensis* IFO-12889 and the present strain have been compared as shown in Table 1. It is seen that except for some difference in the color of aerial mycelia, they show very good agreement in the other microbiological properties.

Hence, the present strain is considered to be a species very similar to *Streptomyces matensis*. But there is a large difference in regard to β-1,3-glucosyl transferase activity. Specifically, the present strain has the activity of transferring glucose from a β-1,3-glucosyl sugar compound to stevioside, whereas *Streptomyces matensis* does not. Furthermore, the optimum growth temperature of the latter is lower. For the foregoing reason, the present strain has been determined to be Streptomyces sp. DIC-108 as a new species analogous to *Streptomyces matensis*.

The present strain was deposited under FERM BP-253 on June 19, 1982 in Fermentation Research Institute, Agency of Industrial Science and Technology, Japan.

TABLE 1

|  | Streptomyces sp. DIC-108 | *Streptomyces matensis* IFO-12889 |
|---|---|---|
| Morphology of the aerial mycelia | Rectinaculliaperti Spiral | Rectinaculliaperti Spiral |
| Surface of the spores | Warty | Warty |
| Color of the aerial mycelia | White gray to greenish gray | White gray to gray |
| Soluble pigment | − | − |
| Melanine pigment | − | − |
| Utilization of carbon sources |  |  |
| D-glucose | + | + |
| L-arabinose | + | + |
| D-xylose | + | + |
| D-fructose | + | + |
| Sucrose | − | − |
| Inositol | + | + |
| Raffinose | − | − |
| D-mannitol | + | + |
| Salicin | − | No description found. |
| Galactose | + | + |
| Liquefaction of gelatin | − | − |
| Coagulation and peptonization of skimmed milk | − | − |

[Microbiological properties of Streptomyces sp. DIC-146]

(1) Morphological characteristics

Good growth on used media (including an ISP medium). Abundant aerial mycelia formed on each medium except on glucose-asparagine agar. Spore chains are spiral. Spores are usually 0.7 to 0.8 μm wide and 1.0 to 1.2 μm long. Spores are oval and their surface is smooth in a scanning electron microphotograph.

(2) Cultural characteristics on various media (1) Sucrose-nitrate agar (37° C.)

Substrate mycelium colorless; grayish brown aerial mycelium; no souble pigment.

(2) Glucose-asparagine agar (37° C.)

Substrate mycelium pale yellow; no aerial mycelium; no soluble pigment.

(3) Glycerol-asparagine agar (ISP medium No. 5, 37° C.)

Substrate mycelium pale grayish brown; violet grayish white aerial mycelium; no soluble pigment.

(4) Starch agar (ISP medium, 37° C.)

Substrate mycelium pale brown; reddish gray aerial mycelium; about 14 days after the start of cultivation, a red pigment formed on the reverse side of the colony.

(5) Tyrosine agar (ISO medium-7, 37° C.)

Substrate mycelium grayish dark brown; brownish grayish white to dark gray aerial mycelium; no soluble pigment.

(6) Nutrient agar (37° C.)

Substrate mycelium grayish brown; grayish white aerial mycelium. About 14 days after the start of cultivation, a red to reddish orange pigment formed on the reverse side of the colony.

(7) Yeast-malt extract agar (ISP medium-2, 37° C.)

Substrate mycelium brown; pale brownish gray aerial mycelium; no soluble pigment.

(8) Oatmeal agar (ISP medium-3, 37° C.)

Substrate mycelium grayish brown; reddish gray aerial mycelium. About 14 days after the start of cultivation, a red pigment formed on the reverse side of the colony.

(3) Physiological properties (1) Growth temperature range

Grows at 30° to 50° C. in a growth test on a yeast extract-malt extract liquid medium, but the optimum temperature is 37° to 45° C.

(2) Liquefaction of gelatin: positive (3) Coagulation and peptonization of skimmed milk: positive (4) Formation of a melanine pigment (peptone-yeast-iron agar medium, ISP medium-6): negative (5) Hydrolysis of starch: negative (6) Utilization of carbon sources (Pridham-Gotlieb agar medium, ISP medium-9, 37° C.)

Grows by well utilizing D-glucose, L-arabinose, D-xylose, D-fructose, inositol, L-rhamnose, raffinose, D-mannitol and galactose. Cannot utilize sucrose and salicin. Or the utilization of sucrose and salicin is doubtful.

(7) Composition of the cell walls

Belongs to type I according to the sugar composition types described in ISP.

From the above characteristics, the present strain is determined to belong to the genus Streptomyces. The color of its aerial mycelia leads to the determination that it is included in gray series and belongs to a non-chromogenic species which does not form a melanine pigment. As a result of investigating known strains for the taxonomical status of the present strain on the basis of the foregoing characteristics, *Streptomyces olivaceus* (International Journal of Systematic Bacteriology, Vol. 18, No. 2, page 154, 1968) can be cited as the most analogous species. *Streptomyces olivaceius* IFO-3409 deposited at Institute of Fermentation Osaka, Japan and the present strain have been cultivated under the same conditions and compared. As shown in Table 2, there is a difference in the color of aerial mycelia on an oatmeal agar medium and a starch inorganic salt agar medium, but they show very good agreement in the other microbiological properties.

Accordingly, the present strain is considered to be a species very analogous to *Streptomyces olivaceus*. But there is a large difference in β-1,3-glucosyl transferase activity. Specifically, the present strain has the activity of transferring glucose from a β-1,3-glucosyl sugar compound to stevioside, whereas *Streptomyces olivaceus* does not. Moreover, the latter has a lower optimum growth temperature. For the foregoing reason, the present strain has been determined to be Streptomyces sp. DIC-146 as a new species analogous to *Streptomyces olivaceus.*

The present strain was deposited under FERM BP-254 on June 19, 1982 in Fermentation Research Institute, Agency of Industrial Science and Technology, Japan.

TABLE 2

| | Streptomyces sp. DIC-146 | Streptomyces olivaceus IFO 3400 |
|---|---|---|
| Morphology of the aerial mycelia | Spiral | Spiral |
| Surface of the spores | Smooth | Smooth |
| Color of the aerial mycelia | White gray to dark gray Reddish gray (Oatmeal agar medium and starch inorganic salt agar medium) | White gray to dark gray |
| Soluble pigment | − (+) (a red pigment formed on the reverse surface of colonies) | − |
| Formation of a melanine pigment | − | − |
| Utilization of carbon sources | | |
| D-glucose | + | + |
| L-arabinose | + | + |
| D-xylose | + | + |
| D-fructose | + | + |
| Sucrose | − (±) | − |
| Inositol | + | + |
| L-rhamnose | + | + |
| Raffinose | + | + |
| D-mannitol | + | + |
| Salicin | − (±) | − |
| Galactose | + | + |
| Liquefaction of gelatin | + | + |
| Coagulation and peptonization of skimmed milk | + | + |

The β-1,3 transferase used in this invention can be obtained by cultivating such a preferred microorganism as exemplified above under aerobic conditions by a conventional method in a liquid culture medium containing known nutrient sources such as carbon sources, nitrogen sources and inorganic components which common microorganisms can utilize.

Examples of the carbon sources include polysaccharides such as starch, amylose, curdlan, pachyman, laminarin and amylopectin, alcohols such as methanol, glycerol and higher alcohols, organic acids such as succinic acid, acetic acid and higher fatty acids, salts of these acids, and sugars such as starch, maltose, glucose and rhamnose. Examples of the nitrogen sources are ammonium sulfate, ammonium chloride, ammonium phosphate, sodium nitrite, urea, peptone and casein.

Examples of natural nutrient sources containing carbon sources, nitrogen sources and other nutrient substances include corn steep liquor, oatmeal, fish meal, meat extract, yeasts, yeast extracts, potato extract and malt extract. Examples of the inorganic materials are dipotassium phosphate, monosodium phosphate, magnesium sulfate and tiny amounts of metals. As required, vitamins may also be added. The concentration of these nutrient sources is 0.1 to 40% by weight. In order to inhibit foaming during fermentation, not more than 1.0% by weight of an antifoamer may also be added. Usual antifoamers such as silicones and soybean oil can be used.

Aerobic liquid cultivation under shaking, aeration, etc. is suitable, and the cultivation is carried out for 1 to 6 days at a pH of 5.0 to 8.0 and a temperature of 20° to 50° C., desirably for about 2 days at a pH of 6.5 to 7.5 and a temperature of 35° to 40° C.

The Streptomyces sp. DIC-108 and DIC-146 used preferably in this invention are industrially useful because their optimum growth temperature is high and they can be cultivated at high temperatures.

The molar conversion of each of the microorganism strains used in this invention is calculated in accordance with the following formula.

$$\frac{\text{Amount of rebaudioside } A \text{ formed}}{\text{Amount of stevioside decreased} \times 1.2} \times 100$$

The "1.2" is calculated as follows:

$$\frac{\text{Molecular weight of rebaudioside } A}{\text{Molecular weight of stevioside}}$$

The microorganism strains used in this invention have a molar conversion of about 50 to 99% which is evidently higher than the conventional value, i.e. 20%. Furthermore, with the microorganism strains in accordance with this invention, the ratio of decrease of stevioside is the same as in the prior art, and the decreased stevioside is converted to rebaudioside A in a high conversion.

The transfer reaction in accordance with this invention is started by adding an enzyme having β-1,3 glucosyl transferase activity or the like or a microorganism capable of producing the enzyme to an aqueous solution containing stevioside and a β-1,3 or β-1,4-glucosyl or galactosyl sugar compound. The concentration of stevioside is about 0.1 to about 10% by weight based on the reaction mixture if it is pure stevioside. The concentration of the β-1,3- or β-1,4-glucosyl or galactosyl sugar compound is adjusted to about 0.1 to about 30% by weight based on the reaction mixture. The pH and temperature of the reaction mixture are such that in the presence of the enzyme or microorganism, β-1,3- or β-1,4-glycosyl stevioside can be formed by the reaction of stevioside with the β-1,3 or β-1,4 sugar compound. Usually, the suitable pH is from 3 to 10, preferably 5 to 8, and the suitable temperature is from 20° to 70° C., preferably 30° to 50° C. The reaction can be carried out either batchwise or continuously.

The resulting reaction solution in which β-1,3- or β-1,4-glycosyl stevioside is thus formed can be directly used as a sweetener. As required, it is possible to inactivate the enzyme or microorganism by heating, remove salts from the solution by using a polymeric adsorbent composed of styrene and divinylbenzene [for example, Diaion HP-20, a trademark for a product of Mitsubishi Chemical Co., Ltd.), Amberlite XAD-2 (a trademark for a product of Organo Co., Ltd.)], or an ion exchange resin (for example, an H-form strongly acidic ion exchange resin or an OH-form weakly basic ion exchange resin), and to concentrate the residue to form a syrupy sweetener, or to dry and powderize it to form a powdery sweetener.

Moreover, the reaction solution after removal of salts can be purified to separate β-1,3- or β-1,4-glycosyl stevioside as a sweetener. The above concentration, drying and powderization can be carried out by known methods such as reduced pressure concentration, membrane concentration, vacuum drying and spray drying.

The sweetness of the $\beta$-1,3- or $\beta$-1,4-glycosyl stevioside so obtained differs depending upon conditions for its measurement. Generally, it is slightly weaker than the sweetness corresponding to the solids weight of stevioside used in the reaction. The quality of its sweetness is such that it is free from unpleasant tastes such as bitterness or astringency and has mild sweetness like sugar. Its aftertaste disappears sharply. In particular, the sweetness of rebaudioside A so obtained has a sweetness about 1.3 times as strong as that corresponding to the solid weight of stevioside used in the reaction. The quality of its sweetness is such that it is free from unpleasant tastes such as bitterness and astringency and has mild sweetness like sugar. Moreover, its aftertaste disappears sharply.

Since these $\beta$-glycosyl stevioside derivatives are odor-free white powders with no bitter and astringent tastes and are soluble in water, they can be used as a liquid or powdery mixture with stevioside or glycyrrhizin in any desired mixing ratios. It is also possible to utilize the taste properties of the $\beta$-glycosyl stevioside derivatives effectively in combination with known synthetic sweetener substances such as saccharin and its salts, sodium cyclamate, dihydrochalcone and aspartame. For example, the addition of a $\beta$-glycosyl stevioside derivative to at least one of these synthetic sweetener substances can result in the removal of the unpleasant tastes such as bitterness and astringency inherent to synthetic sweeteners.

The addition of such a $\beta$-stevioside derivative increases the sweetness of known carbohydrate sweeteners such as sucrose, fructose, glucose, lactose, millet jelly, dextrin and starch, and the amount of these sweeteners used can be decreased greatly. The addition of these compounds can also increase the sweetness of low-calorie sweetener substances having a lower degree of sweetness than sugar, such as sorbitol, maltitol, mannitol and xylitol without impairing the advantages of the favorable properties of these sweeteners, and can provide low-calorie sweeteners of good quality.

$\beta$-Glycosyl steviosides can therefore be used as sources of sweetness in general foods, dietary foods, medicines or cosmetics and like articles, tobacco, animal feeds, etc.

For example, they can be used to sweeten various foods, drinks and articles of luxury, for example various seasonings such as soy sauce, miso, mayonnaise, dressings, vinegar, mixed vinegar, seasonings for Chinese foods, sauce, ketchup, barbecue sauce, curry sauce, stew base, soup base, stock base, compound seasonings, mirin, and table syrup; various confections such as jelly, bread, biscuit, cracker, cookie, pie, pudding, butter cream, custard cream, cream puff, waffle, sponge cake, doughnut, chocolate, chewing gum, caramel and candy; ice confections such as ice cream, sherbet and ice candy; syrups such as fruits preserved in syrups, and peach syrup; pastes such as flower pastes, peanut paste and fruit pastes; processed foods from fruits and vegetables such as jams, marmalade, and sweetmeats; meat products such as hams and sausages; fish meat products such as fish hams and sausages; daily dishes such as potato salad and boiled beans; bottled and canned foods such as fish, meats, fruits and vegetables; wines and liquors; soft drinks such as coffee, cocoa, juices, carbonated beverages, and drinks containing lactic acid and Lactobacilli; and instant foods such as pudding mixes, hot cake mixes, instant juices and instant coffee. They can also be incorporated as sweeteners in various medicines, cosmetics, and like articles, such as dentifrice pastes, rouge, lip cream, internally administrable drugs, troches, liver oil drops, mouth refreshing agents, mouth flavor tablets and gargles.

The process of this invention and the sweeteners obtained by it will be illustrated below specifically by the following examples taken in conjunction with the accompanying drawings. All percentages in these examples are by weight.

EXAMPLE 1

(1) Preparation of $\beta$-1,3 Glucosyl transferase

Streptomyces sp. DIC-108 (FERM BP 253) was inoculated in 5 liters of a culture medium composed of 0.2 w/V % of yeast extract, 0.2 W/V % of polypeptone, 0.5 W/V % of glucose, 0.1 W/V % of $MgSO_4.7H_2O$ and 0.2 W/V % of $K_2HPO_4$. Simultaneously, 100 g of separately sterilized curdlan was added, and the above strain was cultivated under aeration and agitation at 37° C. for 40 hours. The resulting culture broth was centrifuged. To the supernatant, solid ammonium sulfate was added to give 80% saturation. Thus, a crude enzyme specimen (1) having $\beta$-1,3 glucosyl transferase activity was obtained.

The enzyme activity of the specimen was about 1000 units. One unit of enzyme activity denotes the amount of the enzyme (protein) required to form 1 micromole of rebaudioside A when stevioside was reacted at 50° C. for 30 minutes in a 0.1M phosphate buffer (pH 7.0) while maintaining the concentration of stevioside at 0.5%.

(2) Transfer reaction (production of rebaudioside A)

Ten grams of Stevia sweetener (trademark, Stevia-DIC, a product of Dainippon Ink and Chemicals, Inc.), 20 g of curdlan (a product of Wako Pure Chemical Co., Ltd.) and 10 units of the crude enzyme specimen (I) prepared in (1) above were suspended in 1 liter of a 0.1M phosphate buffer (pH 7.0). The suspension was stirred at 50° C. for 30 minutes. The reaction mixture was filtered, and heated at 90° C. for 10 minutes to inactivate the enzyme. The resulting solution was passed through an absorbent resin (Diaion HP-20, a trademark for a product of Mitsubishi Chemical Co., Ltd.) at an S.V. (space velocity) of 2 to cause adsorption of steviosides. Then, the steviosides were removed by using 95% ethanol. After the removal, the ethanol was evaporated under reduced pressure, and the residue was passed at an SV of 2 through a strongly acidic ion exchange resin (Amberlite IR-120B, H type, a trademark for a product of Rohm & Haas Co.) and a weakly basic ion exchange resin (Amberlite IRA-93, OH type, a trademark for a product of Rhom & Haas Co.) to remove salts. The residue was concentrated under reduced pressure at less than 70° C., and dried under vacuum to give a sample No. 2 (to be referred to as an improved sweetener) containing 2.7 g of rebaudioside A and 3.3 g of stevioside in powder form.

As a control (sample No. 1), the same reaction as above was carried out by using a crude enzyme specimen which had been inactivated by heating beforehand. The reaction product was purified by an adsorbent resin and ion-exchange resins to give a product containing 1.4 g of rebaudioside A and 5.2 g of stevioside. A comparison of Sample No. 1 with Sample No. 2 led to the determination that by the action of the crude enzyme specimen (I) of β-1,3-glucosyl transferase, the amount of stevioside decreased by about 36%, and the amount of rebaudioside A increased by about 93%. The molar conversion of this reaction was 57%.

(3) Test for the sweetness of the improved sweetener

Aqueous solutions of samples Nos. 1 and 2 in concentrations of 0.02% and 0.05% were individually prepared. Separately, standard aqueous sugar solutions having various concentrations between 1 to 7% (13 different concentrations differing by 0.5%) were prepared. The test for sweetness was conducted on these solutions. Each of the sample solutions was compared with each of the standard solutions by a panel of 20 members at 20° C. The results are shown in Table 3.

TABLE 3

| | Sample | | | | | |
|---|---|---|---|---|---|---|
| | Sample No. 1 (control) | | | Sample No. 2 (improved sweetener) | | |
| | Comparison of sweetness | | | | | |
| Sugar concentration | Stronger | Same | Weaker | Stronger | Same | Weaker |
| (a) 0.02% aqueous solution | | | | | | |
| 1.0% | 20 | 0 | 0 | 20 | 0 | 0 |
| 1.5% | 18 | 1 | 1 | 18 | 2 | 0 |
| 2.0% | 16 | 2 | 2 | 17 | 3 | 0 |
| 2.5% | 12 | 4 | 4 | 13 | 5 | 2 |
| 3.0% | 7 | 8 | 5 | 10 | 7 | 3 |
| 3.5% | 3 | 3 | 14 | 4 | 9 | 7 |
| 4.0% | 0 | 3 | 17 | 2 | 6 | 12 |
| (b) 0.05% aqueous solution | | | | | | |
| 4.5% | 20 | 0 | 0 | 20 | 0 | 0 |
| 5.0% | 18 | 1 | 1 | 16 | 3 | 1 |
| 5.5% | 11 | 5 | 4 | 11 | 4 | 5 |
| 6.0% | 4 | 10 | 6 | 7 | 5 | 8 |
| 6.5% | 2 | 4 | 12 | 2 | 9 | 9 |
| 7.0% | 0 | 1 | 19 | | | |

It is seen from the results shown in Table 3, (a) and (b) that the sweetness of sample No. 1 as a 0.02% aqueous solution corresponds to a sugar concentration of 3% (sweetness 150 times), and as a 0.05% aqueous solution, to a sugar concentration of 6% (sweetness 120 times). Likewise, the sweetness of sample No. 2 corresponds to a sugar concentration of 3.5% and 6.5% respectively. It was judged therefore that the sweetness of the improved sweetener is about 1.1 to 1.2 times that corresponding to stevioside used.

(4) Test for the quality of the taste of the improved sweetener

The improved sweetener (sample No. 2) and the control (sample No. 1) were compared in regard to the quality of taste. By calculation from the sweetnesses in the sweetness test described above, aqueous solutions of these samples having sweetnesses corresponding to 3%, 6% and 10% aqueous solutions of sugar were prepared. The quality of the taste of the sample No. 1 solution was compared with that of the sample No. 2 solution at each sweetness level.

The test was conducted by a panel of 20 members at 20° C., and the results are shown in Table 4.

TABLE 4

| | Sample | | | | | |
|---|---|---|---|---|---|---|
| | Sample No. 1 (control) | | | Sample No. 2 (improved sweetener) | | |
| Sugar concentration | Quality of sweetness | | | | | |
| | Better | Same | Worse | Better | Same | Worse |
| 3% | 0 | 3 | 17 | 17 | 3 | 0 |
| 6% | 0 | 1 | 19 | 19 | 1 | 0 |
| 10% | 0 | 0 | 20 | 20 | 0 | 0 |

It is seen from the results shown in Table 4 that the quality of the sweetness of the improved sweetener (sample No. 2) is superior to that of sample No. 1 (control) at any sweetness level.

EXAMPLE 2

Separation and determination of rebaudioside A (1) Synthesis from stevioside

Ten grams of pure stevioside, 20 g of curdlan and 10 units of the crude β-1,3 glucosyl transferase specimen (I) obtained in Example 1, (1) were suspended in 1 liter of a 0.1M phosphate buffer (pH 7.0), and reacted at 50° C. for 1 hour with stirring. The reaction mixture was filtered, and then heated at 90° C. for 10 minutes to inactivate the enzyme. The decrease of stevioside by 4.8 g was observed. The solution was passed through 220 ml of a synthetic adsorbent resin (Diaion HP-20) to cause adsorption of steviosides, and the adsorbed steviosides were removed by using 80% ethanol. The solvent was evaporated, and the residue was dried under reduced pressure.

The dried product was dissolved in a solvent consisting of chloroform, methanol and water in a ratio of 30:25:4, and adsorbed on a column of 600 ml of silica gel (Wakogel C-300, tradename for a product of Wako Pure Chemical, Co. Ltd.). The column was then developed with the aforesaid solvent to recover fractions corresponding to rebaudioside A. The fractions were concentrated to dryness under reduced pressure to give 3.5 g of a white powder corresponding to rebaudioside A (the product is referred to as sample No. 3).

The mole conversion of this reaction was 60%.

(2) Extraction of natural rebaudioside A

Separately, 150 g of dried Stevia leaves were extracted twice with 3 liters of warm water (50° C.) for 3 hours and the extract was concentrated to 3 liters. Proteins were removed from the extract, and the residue was passed through a column packed with 400 ml of a synthetic adsorbent resin (Diaion HP-21) at an S.V. of 2.0 to cause adsorption of steviosides. Thereafter, 750 ml of 95% ethanol was passed through the column at an S.V. of 2.0 to remove the steviosides. Ethanol was evaporated under reduced pressure, and the resulting dried product was dissolved in 600 ml of water. The solution was passed through a column packed with 130 ml of a strongly acidic ion exchange resin (IR-120B, H form) at an S.V. of 2.0, and then through a column packed with a weakly basic ion exchange resin (IRA-93, OH form) at an S.V. of 2.0 to remove salts. The residue was then concentrated under reduced pressure at less than 70° C., and dried under vacuum to give about 20 g of purified powdery Stevia (trademark, Stevia-DIC). The purified Stevia was dissolved in 5 times (W/W) its amount of hot methanol (60° C.). The solution was then cooled, and the precipitate was collected by filtration. The filtrate was dried under reduced pressure, and 10 g of the resulting product was chromatographed on a column of Wako Gel C-300.

The column was eluted with a mixed solvent consisting of chloroform, methanol and water in a ratio of 6.5:3:1 (V/V/V), and 1.16 g of stevioside and 0.7 g of rebaudioside A were isolated.

Figure 2:
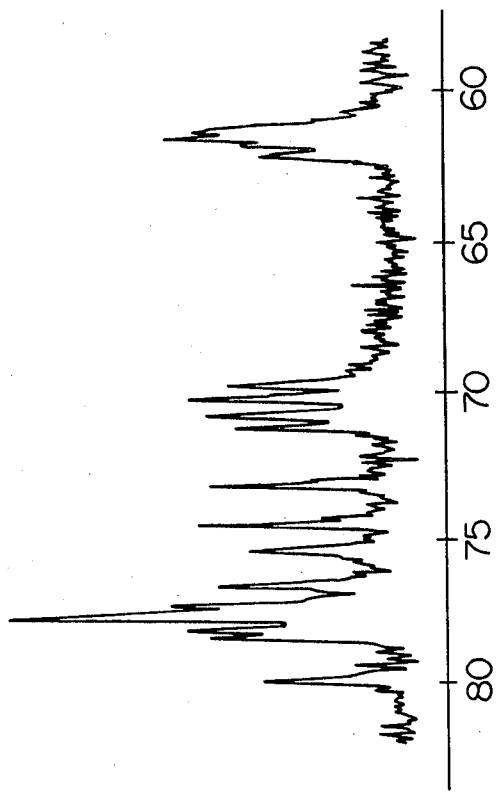
FIG. 2 is a partially enlarged view of FIG. 1.

Analysis by high-performance liquid chromatography showed that sample No. 3 had the same retention time as rebaudioside A. Sample No. 3 was spotted on a silica gel 60F plate (a product of Merck & Co.) and developed with a solvent composed of chloroform, methanol and water (30:20:4). The spot of sample No. 3 corresponded with rebaudioside A showing an Rf value of 0.84 when the Rf value of stevioside was taken as 1. When the structure of sample No. 3 was identified by $^{13}$C-NMR, the data obtained corresponded with the data of rebaudioside A described by Tanaka et al. Tetrahedron Letters, No. 13, 1005, 1976). (See Table 5, FIGS. 1 and 2.)

The foregoing results led to the confirmation that sample No. 3 obtained by the action of the crude $\beta$-1,3 glucosyl transferase specimen on stevioside and curdlan as substrates was rebaudioside A.

The melting point of sample No. 3 was found to be 237° to 239° C.

TABLE 5

| | | $^{13}$C-NMR Data | |
|---|---|---|---|
| | | Rebaudioside A* | Sample No. 2 |
| C- | 1 | 40.9 | 40.8 |
| | 2 | 19.4 | 19.3 |
| | 3 | 38.3 | 38.4 |
| | 4 | 44.0 | 44.0 |
| | 5 | 57.4 | 57.4 |
| | 6 | 22.2 | 22.1 |
| | 7 | 41.8 | |
| | 8 | 42.4 | 42.4 |
| | 9 | 54.0 | 54.0 |
| | 10 | 39.8 | 39.8 |
| | 11 | 20.7 | 20.5 |
| | 12 | 37.3 | 36.7 |
| | 13 | 86.6 | 86.5 |
| | 14 | 44.5 | 44.5 |
| | 15 | 47.9 | 47.7 |
| | 16 | 153.9 | 153.8 |
| | 17 | 104.5 | 104.5 |
| | 18 | 28.3 | 28.3 |
| | 19 | 177.0 | 176.9 |
| | 20 | 15.5 | 15.5 |
| G- | 1 | 95.6 | 95.6 |
| | 2 | 73.8 | 73.8 |
| | 3 | 78.8 | 79.0 |
| | 4 | 70.8 | 70.9 |
| | 5 | 78.8 | 78.7 |
| | 6 | 62.3 | 62.3 |
| G1- | 1 | 97.9 | 97.9 |
| | 2 | 80.7 | 80.5 |
| | 3 | 87.8 | 87.8 |
| | 4 | 70.5 | 70.5 |
| | 5 | 78.3 | 78.4 |
| | 6 | 62.3 | 62.3 |
| G2- | 1 | 104.5 | 104.5 |
| G3- | 1 | 104.5 | 104.5 |

*K. Yamasaki, H. Kohda, T. Kobayashi, R. Kasai and O. Tanaka, Tetrahedron Letters, No. 13, 1005 (1976).

The measuring conditions were in accordance with the above cited reference. Specifically, they were as follows:
Instrument: JEOL PX-100-NMR, 25.05 MNz
Measuring temperature: Room temperature
Solvent: $C_5D_5N$
Internal standard: TMS
Concentration: 200 mg/1 ml (S), 100 mg/0.7 ml (R)

Spectral width: 5 KHz
Pulse width: 7 sec (30° C.)
Data point: 8192
Pulse repetition (PR): 3 sec
Number of additions: 3400 (R), 5000 (S)

EXAMPLE 3

Streptomyces sp. DIC-146 (FERM BP-254) was inoculated in 5 liters of a culture medium having the same composition as in Example 1, (1), and cultivated under aeration and agitation at 37° C. for 40 hours in the same way as in Example 1. The culture broth was centrifuged, and to the supernatant solid ammonium sulfate was added to give 80% saturation. Thus, a crude enzyme specimen (II) having $\beta$-1,3-glucosyl transferase activity was obtained. The enzyme activity was about 910 units.

Ten grams of Stevia-DIC (containing 51% of stevioside and 14.5% of rebaudioside A), 10 g of curdlan and 9.1 units of the resulting crude enzyme (II) were suspended in 1 liter of a 0.1M phosphate buffer (pH 7.0), and reacted at 50° C. for 2 hours. The reaction mixture was purified by an adsorbent resin and then dried in the same way as in Example 1, (1). Analysis by high-performance liquid chromatography showed that 11.5 g of a white solid containing 32% of stevioside and 26% of rebaudioside A was obtained.

The molar conversion of stevioside to rebaudioside A was about 94%.

EXAMPLE 4

Five hundred milliliters of an aqueous extract of Stevia leaves (containing about 74% of stevioside and 14.5% of rebaudioside A) instead of Stevia-DIC and 100 g of curdlan were added to a 0.1M phosphate buffer (pH 7.0) so that the total amount became 5.0 liters. Then, 50 units of the crude enzyme specimen prepared in Example 1, (1) was added, and the mixture was stirred at 40° C. for 4 hours. The reaction mixture was filtered, and then heated at 90° C. for 10 minutes to inactivate the enzyme. The resulting solution was passed through ion-exchange resins (Amberlite IR-120B and IRA-93) to remove impurities in the Stevia leaf extract. The product contained 25% of rebaudioside A. This amount of rebaudioside A was about 1.7 times as large as that in the original Stevia leave extract.

EXAMPLE 5

(1) Transfer reaction (production of $\beta$-1,3 glucosyl stevioside)

Forty grams of curdlan (a product of Wako Pure Chemical, Co., Ltd.) and 2.5 g of DRISELASE (trademark for a product of Kyowa Hakko Co., Ltd.) instead of the crude enzyme specimen (I) used in Example 1, (2) were suspended in 1 liter of a 0.1M citrate buffer (pH 4.5), and reacted at 50° C. for 2 hours with stirring. Otherwise, the same procedure as in Example 1 was carried out to give $\beta$-1,3 glucosyl stevioside (to be referred to as an improved sweetener) (sample No. 5).

As a control, the same reaction as above was carried out by using DRISELASE which had been inactivated by heating beforehand. The crude product was purified to obtain sample No. 4.

(2) Test for the sweetness of the improved sweetener

Aqueous solutions of samples Nos. 4 and 5 having a concentration of 0.02% and 0.05% respectively were prepared, and the same sweetness test as in Example 1 was conducted. The results are shown in Table 6.

TABLE 6

| | Sample | | | | | |
|---|---|---|---|---|---|---|
| | Sample No. 4 (control) | | | Sample No. 5 (improved sweetener) | | |
| | Comparison of sweetness | | | | | |
| Sugar concentration | Stronger | Same | Weaker | Stronger | Same | Weaker |
| (a) 0.02% aqueous solution | | | | | | |
| 1.0% | 20 | 0 | 0 | 20 | 0 | 0 |
| 1.5% | 18 | 1 | 1 | 18 | 1 | 1 |
| 2.0% | 15 | 3 | 2 | 16 | 2 | 2 |
| 2.5% | 12 | 4 | 4 | 12 | 5 | 3 |
| 3.0% | 7 | 7 | 6 | 6 | 8 | 6 |
| 3.5% | 3 | 3 | 14 | 3 | 4 | 13 |
| 4.0% | 0 | 3 | 17 | 0 | 2 | 18 |
| (b) 0.05% aqueous solution | | | | | | |
| 4.5% | 20 | 0 | 0 | 20 | 0 | 0 |
| 5.0% | 17 | 2 | 1 | 16 | 2 | 2 |
| 5.5% | 11 | 5 | 4 | 13 | 4 | 3 |
| 6.0% | 5 | 9 | 6 | 5 | 10 | 5 |
| 6.5% | 2 | 4 | 12 | 1 | 5 | 14 |
| 7.0% | 0 | 1 | 19 | | | |

It is seen from the results given in Table 6, (a) and (b) that the sweetness of sample No. 4 as a 0.02% aqueous solution corresponds to a sugar concentration of 3% (sweetness 150 times), and as a 0.05% aqueous solution, to a sugar concentration of 6% (sweetness 120 times). On the other hand, the sweetness of sample No. 5 corresponds to a sugar concentration of 3.0% and 6.0%, respectively. It is judged therefore that the sweetness of the improved sweetener is the same as the sweetness corresponding to the stevioside used.

(3) Test for the quality of the taste of the improved sweetener

In the same way as in Example 1, the quality of the sweetness of sample No. 5 was compared with that of sample No. 4 (control). The results are shown in Table 7.

TABLE 7

| | Sample | | | | | |
|---|---|---|---|---|---|---|
| | Sample No. 4 (control) | | | Sample No. 5 (improved sweetener) | | |
| | Quality of sweetness | | | | | |
| Sugar concentration | Better | Same | Worse | Better | Same | Worse |
| 3% | 0 | 5 | 15 | 15 | 5 | 0 |
| 6% | 0 | 2 | 18 | 18 | 2 | 0 |
| 10% | 0 | 0 | 20 | 20 | 0 | 0 |

It is seen from the results given in Table 7 that the quality of the sweetness of the improved sweetener (sample No. 5) is superior to the control (sample No. 4) at any sweetness level.

EXAMPLE 6

(1) Separation and determination of $\beta$-1,3-glucosyl stevioside

Stevioside (5.0 g), 5.0 g of curdlan and 0.25 g of DRISELASE were suspended in 200 ml of a 0.1M citrate buffer (pH 4.5), and the suspension was stirred at 50° C. for 2 hours. The reaction mixture was filtered and then heated at 80° C. for 10 minutes to inactivate the enzyme. The solution was passed through 200 ml of a synthetic adsorbent resin (Diaion HP-20) to cause adsorption of steviosides. Then, the steviosides were removed by using 80% ethanol. The solvent was evaporated, and the residue was dried under reduced pressure.

The dried product was dissolved in a mixed solvent consisting of chloroform, methanol and water in a ratio of 30:25:4, and the solution was adsorbed on a 600 ml silica gel column (Wakogel C-300, a tradename for a product of Wako Pure Chemical, Co., Ltd.). The column was developed with the aforesaid mixed solvent, and fractions corresponding to $\beta$-1,3-glycosyl stevioside were collected. The fractions were concentrated to dryness under reduced pressure to give 3.0 g of a white powder.

It was found that when laminarinase was caused to act on $\beta$-1,3-glucosyl stevioside, it was decomposed to $\beta$-D-glucose and stevioside. It was determined therefore that the substance obtained was $\beta$-1,3-glucosyl stevioside resulting from the $\beta$-1,3 bonding of $\beta$-D-glucose to stevioside.

(2) Test for the sweetness of $\beta$-1,3-glucosyl stevioside

Aqueous solutions of $\beta$-1,3-glucosyl stevioside collected by column chromatography in a concentration of 0.02% and 0.05% were prepared. Separately, standard aqueous sugar solutions having a concentration of 1.5 to 6% (ten different concentrations differing by 0.5%) were prepared. Using these solutions, a sweetness test was conducted in the same way as in Example 1. The results are shown in Table 8.

TABLE 8

| | Sample | | |
|---|---|---|---|
| | $\beta$-1,3-glucosyl stevioside | | |
| Sugar concentration | Comparison of sweetness | | |
| | Stronger | Same | Weaker |
| (a) 0.02% aqueous solution | | | |
| 1.5% | 18 | 2 | 0 |
| 2.0% | 12 | 6 | 2 |
| 2.5% | 7 | 7 | 8 |
| 3.0% | 3 | 4 | 13 |
| 3.5% | 1 | 2 | 17 |
| (b) 0.05% aqueous solution | | | |
| 3.5% | 19 | 1 | 0 |
| 4.0% | 16 | 3 | 1 |
| 4.5% | 13 | 4 | 3 |
| 5.0% | 5 | 9 | 6 |
| 5.5% | 3 | 5 | 12 |
| 6.0% | 1 | 2 | 17 |

It was judged from the results given in Table 8 that the sweetness of $\beta$-1,3-glucosyl stevioside as a 0.02% aqueous solution corresponds to a sugar concentration of 2.5% (sweetness 125 times), and as a 0.05% aqueous solution, to a sugar concentration of 5.0% (sweetness 100 times).

(3) Test for the quality of the taste of $\beta$-1,3-glucosyl stevioside

Pure stevioside (control) was compared with $\beta$-1,3-glucosyl stevioside in the quality of sweetness in the same way as in Example 1. The results are shown in Table 9.

TABLE 9

| | Sample | | | | | |
|---|---|---|---|---|---|---|
| Sugar concentration (%) | Pure stevioside | | | $\beta$-1,3-glucosyl stevioside | | |
| | Quality of sweetness | | | | | |
| | Better | Same | Worse | Better | Same | Worse |
| 3 | 0 | 3 | 17 | 17 | 3 | 0 |
| 6 | 0 | 1 | 19 | 19 | 1 | 0 |

TABLE 9-continued

| Sugar concentration (%) | Sample | | | | | |
|---|---|---|---|---|---|---|
| | Pure stevioside | | | β-1,3-glucosyl stevioside | | |
| | Quality of sweetness | | | | | |
| | Better | Same | Worse | Better | Same | Worse |
| 10 | 0 | 0 | 20 | 20 | 0 | 0 |

It is seen from the results given in Table 9 that the quality of the sweetness of β-1,3-glucosyl stevioside is superior to stevioside at any sweetness level. According to the senses of the panelists, β-1,3 glucosyl stevioside is free from the defect of persisting unpleasant tastes such as bitterness and astringency and has mild sweetness with sharp disappearance of after-taste which is comparatively close to the sweetness of sugar.

EXAMPLE 7

Ten grams of Stevia DIC 90HP (containing 90% of steviosides), 10 g of curdlan and 0.5 g of laminarinase were suspended in 500 g of a 0.1M citrate buffer (pH 5.0). The suspension was stirred at 36° C. for 24 hours. The reaction mixture was purified on an adsorbent resin in the same way as in Example 1, and then dried to give 12 g of a white solid.

Analysis by high-performance liquid chromatography showed that the peak area ratio corresponding to β-1,3 glucosyl stevioside increased to 45% from 20% for Stevia DIC 90HP. By a test for taste, a decrease in bitterness was observed.

EXAMPLE 8

Stevioside (2.0 g), 2.0 g of curdlan and 50 mg of ZYMOLYASE 500 (a tradename for a product of Seikagaku Kogyo Co., Ltd.) were suspended in a 0.1M phosphate buffer (pH 7) and reacted at 36° C. for 6 hours. When the reaction mixture was analyzed by high-performance liquid chromatography, 0.5 g of β-1,3-glycosyl stevioside was found to be formed.

EXAMPLE 9

One hundred milliliters of a culture medium (pH 7.0) composed of 0.2% of yeast extract, 0.2% of polypeptone, 0.1% of $MgSO_4.7H_2O$, 0.2% of $K_2HPO_4$ and 0.5% of glucose was placed in a 500 ml Sakaguchi flask, sterilized by autoclaving (120° C., 10 minutes), and allowed to cool. Then, 0.3 g of laminarin was aseptically added. *Bacillus coagulans* ATCC 21366 was inoculated in the culture medium, and cultivated at 37° C. for 20 hours with shaking. The culture broth was adjusted to pH 7.0 with 1N potassium hydroxide, and 0.5 g of stevioside and 2.0 g of curdlan were added. The mixture was shaken further for 40 hours to perform a transfer reaction. After the reaction, the reaction mixture was heated at 90° C. for 10 minutes, cooled, and then centrifuged (8,000 rpm × 10 minutes) to remove the cells. The supernatant liquid was analyzed by high-performance liquid chromatography. It was found that the amount of stevioside decreased to 0.38 g, and 55 mg of β-1,3-glucosyl stevioside was obtained.

EXAMPLE 10

4.0 Liters of the same culture medium as used in Example 9 was charged into a 10-liter jar fermentor, and sterilized by autoclaving (120° C., 30 minutes). After cooling, 15 g of curdlan instead of laminarin used in Example 9 was added aseptically. Then, 200 ml of a seed culture broth of *Arthrobacter luteus* ATCC 21606 which had been cultivated in the same culture medium at 30° C. for 20 hours was inoculated in the culture medium prepared as above, and cultivated at 30° C. for 18 hours with stirring at 600 rpm while passing air at a flow rate of 5.0 liters/min. Then, 50 g of Stevia DIC 90HP (dissolved in 800 ml of tap water) and 100 g of curdlan which had been separately sterilized were added to perform a transfer reaction. After a reaction period of 20 hours, the reaction mixture was centrifuged to remove the cells. The supernatant liquid was analyzed by high-performance liquid chromatography. It was found that the peak area ratio corresponding to β-1,3-glucosyl stevioside increased to 52% from 20% for Stevia DIC 90HP. In a test for taste, a decrease in bitterness was evidently observed.

Some examples of using the sweetener obtained by the process of this invention are given as Application Examples.

Application Example 1

A powdery juice was prepared on a trial basis in accordance with the following formulation.

| | |
|---|---|
| Granular sugar | 939 g |
| Citric acid | 29 g |
| Sodium citrate | 21 g |
| Malic acid | 14 g |
| Fragrance | 11 g |
| β-Carotene (1.5%) | 3 g |
| Improved sweetener of the invention | 2.5 g |

As a comparison, a powdery juice was prepared as above except that 2.5 g of stevioside powder (90% pure) was added instead of the improved sweetener in the above formulation. A taste test by a panel of 20 members showed that the powdery juice of this invention was quite free from bitterness and astringency, but the comparative juice showed persisting bitterness.

Application Example 2

An orange juice containing 20% of natural orange juice was prepared on a trial basis in accordance with the following formulation.

| | |
|---|---|
| 100% Natural orange juice | 440 g |
| High-quality refined suger | 20 g |
| High-isomerized fructose | 213 g |
| Citric acid | 4 g |
| Sodium citrate | 0.4 g |
| Fragrance | 2 g |
| Malic acid | 2 g |
| β-Carotene (1.5%) | 0.6 g |
| Improved sweetener | 0.3 g |
| Water to make | 2 liters |

As a comparison, an orange juice was prepared on a trial basis as above except that 0.3 g of stevioside powder (90%) was added instead of the improved sweetener in the above formulation. A taste test by a panel of 20 members showed that the product of this invention had mild sweetness and flavor, but the comparative product showed an unpleasant aftertaste.

Application Example 3

Cider was prepared on a trial basis in accordance with the following formulation.

| | |
|---|---|
| Granular sugar | 34 g |
| Isomerized sugar | 180 g |
| Citric acid | 4 g |
| Sodium citrate | 0.2 g |
| Cider essence | 0.2 g |
| Improved sweetener | 0.25 g |
| Carbonated water to make | 2 liters |

A comparative product was prepared as above except that 0.25 g of stevioside powder (90%) was added instead of the improved sweetener in the above formulation. A taste test by a panel of 20 members showed that the product of the invention had light sweetness with sharp disappearance of aftertaste, but the comparative product had bitterness and astringency.

EXAMPLE 11

(1) Preparation of yeast cell (preparation of β-1,4-glucosyl tranferase)

3.0 Liters of a culture medium (pH 5.2) composed of 0.4% of monopotassium phosphate, 0.5% of ammonium sulfate, 0.06% of magnesium sulfate, 0.001% of zinc sulfate, 0.005% of ferrous sulfate, 0.1% of yeast extract and 1% of glucose was charged into a 10-liter jar fermentor. *Rhodotorula minuta* (IFO-1540) was inoculated in the culture medium, and cultivated at 30° C. for 24 hours with aeration and agitation. The resulting culture broth was centrifuged, and the microbial cells obtained were washed two times with a 0.05M phosphate buffer, and then suspended in 600 ml of the same buffer to prepare a suspension (I) of resting cells.

(2) Transfer reaction (production of β-1,4 glucosyl stevioside)

Eighty grams of purified stevioside (Stevia-DIC) and 80 g of cellobiose were dissolved in 3.4 liters of a 0.05M phosphate buffer (pH 6.0), and the suspension (I) of resting cells was added to form 4 liters of a mixture which was then reacted at 37° C. for 96 hours. The reaction mixture was purified in the same way as in Example 1, (2) to obtain an improved sweetener in powder form (sample No. 7).

As a control, the same reaction as above was carried out using the microbial cells which had been inactivated in advance by heating, and the reaction mixture was purified by using an adsorbent resin and an ion exchange resin to obtain a sweetener (sample No. 6).

(3) Test for the sweetness of an improved sweetener

Aqueous solutions of samples Nos. 6 and 7 in concentrations of 0.02 and 0.05% were prepared, and the same sweetness test as in Example 1 was conducted. The results are shown in Table 10.

TABLE 10

| Sugar concentration (%) | Sample No. 6 (control) | | | Sample No. 7 (improved sweetener) | | |
|---|---|---|---|---|---|---|
| | Comparison of sweetness | | | | | |
| | Stronger | Same | Weaker | Stronger | Same | Weaker |
| (a) 0.02% aqueous solution | | | | | | |
| 1.0 | 20 | 0 | 0 | 20 | 0 | 0 |
| 1.5 | 18 | 2 | 1 | 16 | 2 | 2 |
| 2.0 | 15 | 3 | 2 | 12 | 5 | 3 |
| 2.5 | 12 | 4 | 4 | 5 | 8 | 7 |
| 3.0 | 7 | 7 | 6 | 3 | 4 | 13 |
| 3.5 | 3 | 3 | 14 | 2 | 3 | 15 |

TABLE 10-continued

| Sugar concentration (%) | Sample No. 6 (control) | | | Sample No. 7 (improved sweetener) | | |
|---|---|---|---|---|---|---|
| | Comparison of sweetness | | | | | |
| | Stronger | Same | Weaker | Stronger | Same | Weaker |
| 4.0 | 0 | 3 | 17 | 0 | 0 | 20 |
| (b) 0.05% aqueous solution | | | | | | |
| 4.0 | | | | 17 | 2 | 1 |
| 4.5 | 20 | 0 | 0 | 13 | 4 | 3 |
| 5.0 | 17 | 2 | 1 | 5 | 10 | 5 |
| 5.5 | 11 | 5 | 4 | 5 | 5 | 10 |
| 6.0 | 5 | 9 | 6 | 0 | 2 | 18 |
| 6.5 | 2 | 4 | 12 | 0 | 0 | 20 |
| 7.0 | 0 | 1 | 19 | | | |

It is seen from the results given in Table 10, (a) and (b) that the sweetness of sample No. 6 as a 0.02% aqueous solution corresponds to a sugar concentration of 3% (sweetness 150 times), and as a 0.05% aqueous solution, to a sugar concentration of 6% (sweetness 120 times). On the other hand, the sweetness of sample No. 7 corresponds to a sugar concentration of 2.5% and 5%, respectively. Hence, it is judged that the sweetness of the improved sweetener is slightly weaker than the sweetness corresponding to the stevioside used.

(4) Test for the taste of the improved sweetener

The improved sweetner (sample No. 7) was compared with the control (sample No. 6) in regard to the quality of sweetness in the same say as in Example 1. The results are shown in Table 11.

TABLE 11

| Sugar concentration (%) | Sample No. 6 (control) | | | Sample No. 7 (improved sweetener) | | |
|---|---|---|---|---|---|---|
| | Quality of sweetness | | | | | |
| | Better | Same | Worse | Better | Same | Worse |
| 3 | 0 | 5 | 15 | 15 | 5 | 0 |
| 6 | 0 | 2 | 18 | 18 | 2 | 0 |
| 10 | 0 | 0 | 20 | 20 | 0 | 0 |

It is seen from the results given in Table 11 that the quality of the sweetness of the improved sweetener (sample No. 7) is superior to the control (sample No. 6) at any sweetness level.

(5) Separation and determination of β-1,4 glucosyl stevioside

Figure 3:
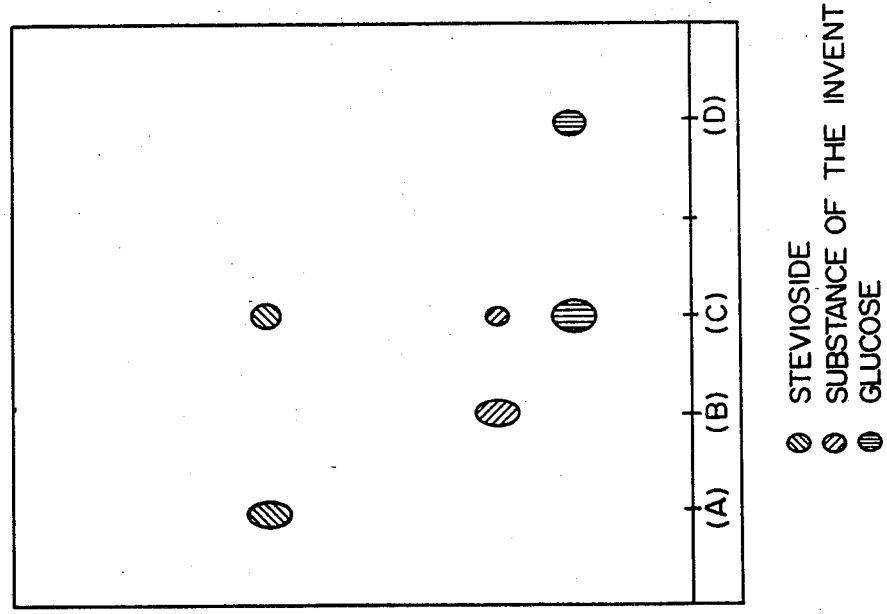
FIG. 3 shows a thin-layer chromatography, in which (A), (B), (C) and (D) respectively represent stevioside, β-1,4-glucosyl stevioside, a β-glucosidase-treated product of (B), and glucose.

The transfer reaction product (improved sweetener) obtained as above was purified by an adsorbent resin and an ion-exchange resin, concentrated under reduced pressure, dried in vacuum, and dissolved in a mixed solvent composed of chloroform, methanol and water in a ratio of 30:25:4. The solution was chromatographed on a column filled with Wakogel C-200 (silica gel made by Wako Pure Chemical Co., Ltd.). The column was eluted with the aforesaid solvent to give various fractions. As a result, fractions regarded as dulcoside A, stevioside, rebaudioside C and rebaudioside A were extracted in this sequence, and finally a fraction considered to be β-1,4-monoglucosyl stevioside was extracted. The last fraction was concentrated under reduced pressure, and dried in vacuum to give a white powder. One milliliter of an about 2% aqueous solution of the resulting powder was taken into a test tube, and β-glucosidase (a product of Sigma Co., Ltd.) was added in a concentration of 0.1%. Then, the reaction was carried out at 37° C. for 7 hours. After the reaction, the resulting product was spotted on a silica gel plate 60F (a product of Merck & Co.). As a control, stevioside, the substance of the invention before treatment with β-glucosidase, and D-glucose were also spotted. Then, the plate was developed with a mixed solvent composed of chloroform, methanol and water in a ratio of 30:20:4. After full air-drying, concentrated sulfuric acid containing 0.2% of anisaldehyde was sprayed onto the plate and heated at 100° C. for 10 minutes to induce coloration. The resulting chromatogram is shown in FIG. 3. It is seen from FIG. 3 that in the case of the sample (C) obtained by treatment with β-glucosidase, a spot at an Rf value of 0.66 ascribed to stevioside (A) and a spot at an Rf value of 0.30 acribed to D-glucose (D) appeared. In the case of the substance (B) of this invention used as a control, a spot was observed only at an Rf value of 0.37.

Figure 4:
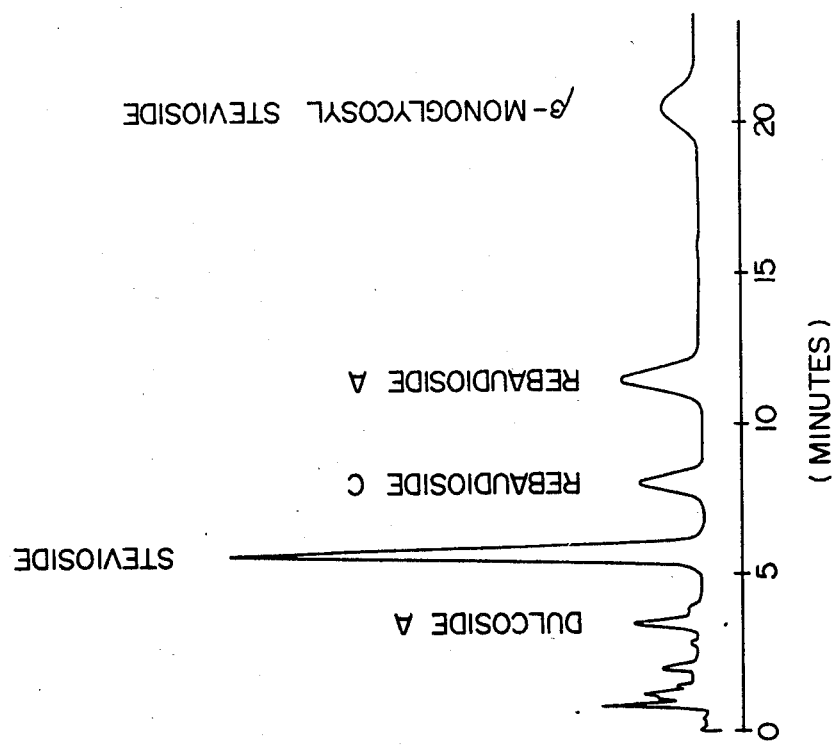
FIG. 4 shows a high-performance liquid chromatographic chart of a β-glucosyl transferase-treated product of stevioside.
Figure 5:
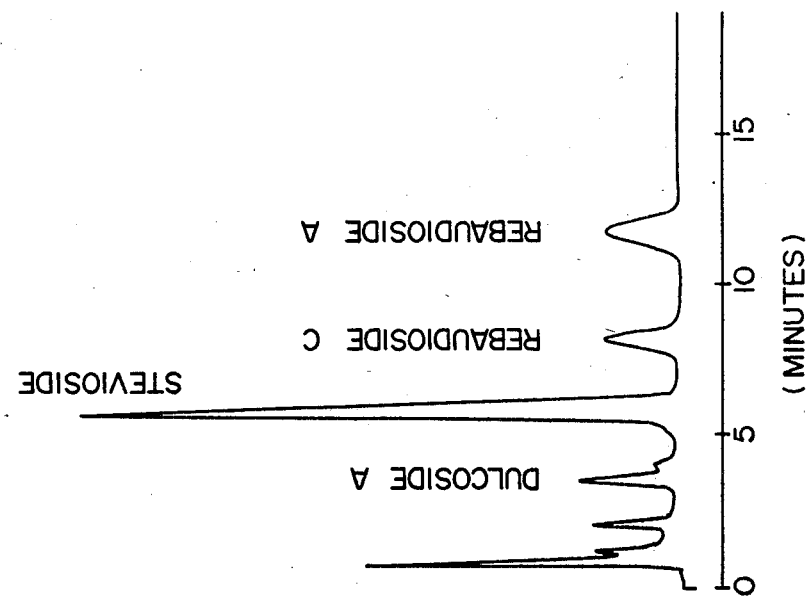
FIG. 5 is a high-performance liquid chromatographic chart of stevioside.

The reaction mixture was analyzed under the following conditions by high-performance liquid chromatography (Model LC-3A, made by Shimazu Seisakusho Co. Ltd.). The results are shown in FIG. 4. In addition to the peaks seen in the raw materials before the reaction (FIG. 5), a new product, β-1,4 glucosyl stevioside, was determined at r.t 20.67 minutes.

Analyzing conditions for high-performance liquid chromatography

| | |
|---|---|
| (1) Column: | Lichrosorb-NH$_2$ 4φ × 150 |
| (2) Moving phase: | CH$_3$CN:water = 81:19 (by volume) |
| (3) Flow rate: | 2 ml/min. |
| (4) Pressure: | 30 kg/cm$^2$ |
| (5) Wavelength: | 200 nm |

These results led to the determination that the substance newly formed by the reaction was a substance in which an equimolar proportion of D-glucose is bonded at β-1,4 to stevioside, i.e., β-1,4-monoglucosyl stevioside.

(6) Test for the sweetness of β-1,4-glucosyl stevioside

Aqueous solutions of β-1,4-glucosyl stevioside collected by column chromatography were prepared in concentrations of 0.02 and 0.05%, and the same sweetness test as in Example 1 was conducted. The results are shown in Table 12.

TABLE 12

| | Sample β-1,4-glucosyl stevioside Comparison of sweetness | | |
|---|---|---|---|
| Sugar concentration | Stronger | Same | Weaker |
| (a) 0.02% aqueous solution | | | |
| 1.0% | 18 | 2 | 0 |
| 1.5% | 12 | 6 | 2 |
| 2.0% | 7 | 7 | 8 |
| 2.5% | 3 | 4 | 13 |
| (b) 0.05% aqueous solution | | | |
| 2.0% | 19 | 1 | 0 |
| 2.5% | 16 | 3 | 1 |
| 3.0% | 13 | 4 | 3 |
| 3.5% | 5 | 9 | 6 |
| 4.0% | 3 | 5 | 12 |

It is judged from the results given in Table 12 that the sweetness of β-1,4-glucosyl stevioside as a 0.02% aqueous solution corresponds to a sugar concentration of 2% (sweetness 100 times), and as a 0.05% aqueous solution, to a sugar concentration of 3.5% (sweetness 70 times).

(7) Test for the quality of the taste of β-1,4-glucosyl stevioside

β-1,4-Glucosyl stevioside was compared with pure stevioside (control) in regard to the quality of sweetness in the same way as in Example 1. The results are shown in Table 13.

TABLE 13

| | Sample | | | | | |
|---|---|---|---|---|---|---|
| | Pure stevioside | | | β-1,4-glucosyl stevioside | | |
| Sugar | Comparison of sweetness | | | | | |
| concentration | Better | Same | Worse | Better | Same | Worse |
| 3% | 0 | 3 | 17 | 17 | 3 | 0 |
| 6% | 0 | 1 | 19 | 19 | 1 | 0 |
| 10% | 0 | 0 | 20 | 20 | 0 | 0 |

It is seen from the results given in Table 13 that the quality of the sweetness of β-1,4-glucosyl stevioside is superior to that of stevioside at any sweetness level. According to the senses of the panelists, β-1,4-glucosyl stevioside does not have the defect of unpleasant aftertastes such as bitterness and astringency as in stevioside, and has mild sweetness with sharp disappearance of aftertaste, which is comparatively close to sugar.

EXAMPLE 12

One hundred milliliters of a culture medium (pH 6.0) composed of 1% of glucose, 0.5% of polypeptone, 0.3% of yeast extract and 0.3% of malt extract was put in a 500 ml Sakaguchi flask and sterilized. Then, *Rhodotorula marina* IFO-1421 was inoculated in the medium, and cultivated at 30° C. for 48 hours with shaking.

The culture broth was centrifuged, and the microbial cells were collected. The microbial cells were washed with a 0.05M phosphate buffer (pH 7.2) at least two times, and then suspended in 20 ml of the same buffer to prepare a suspension (II) of resting cells as a source of β-glucosyl tranferase.

Separately, 30 ml of a 0.05M acetic acid-sodium acetate buffer (pH 5.0) was put in a 500 ml Sakaguchi flask, and 0.5 g of purified stevioside (Stevia-DIC) and 0.5 g of cellobiose were dissolved in the buffer. Then, the solution was sterilized by autoclaving.

The suspension (II) of the resting cells prepared as above was added to the reaction solution, and the reaction was carried out at 37° C. for 48 hours at a final pH of 6.0. The cells were removed, and the resulting reaction mixture was a mixed solution of stevioside, rebaudioside C, rebaudioside A, and β-1,4-glucosyl stevioside resulting from the β-1,4-glucosylation of about 25% of stevioside. The mixed solution was purified in the same way as in Example 1, concentrated, and dried to give an improved sweetener. The resulting sweetener showed the same degree and quality of sweetness as in Example 11.

EXAMPLE 13

Production of β-1,4-galactosyl stevioside (1) Eighty grams of purified stevioside (Stevia-DIC) and 160 g of lactose were dissolved in 3.4 liters of a 0.05M phosphate buffer (pH 6.0), and the solution was charged into a 10-liter jar fermentor. After sterilization and cooling, the suspension (II) of resting cells obtained in Example 12 was added to give 4 liters of a mixture.

The mixture was then reacted at 37° C. for 96 hours. After the reaction, the reaction mixture was heated to inactivate the enzyme, and then purified in the same way as in Example 1-(2) to give an improved sweetener in powder form (sample No. 9).

As a control, the above reaction was carried out except that the cells which had been inactivated by heating in advance were used. The reaction mixture was purified by using an adsorbent resin and an ion-exchange resin to give a control sample (sample No. 8).

(2) Test for the sweetness of the improved sweetener

Aqueous solutions of samples Nos. 8 and 9 in concentrations of 0.02 and 0.05% respectively were prepared, and the same sweetness test as in Example 1 was conducted. The results are shown in Table 14.

TABLE 14

| Sugar concentration | Sample No. 8 (control) | | | Sample No. 9 (improved sweetener) | | |
|---|---|---|---|---|---|---|
| | Stronger | Same | Weaker | Stronger | Same | Weaker |
| (a) 0.02% aqueous solution | | | | | | |
| 1.0% | 20 | 0 | 0 | 20 | 0 | 0 |
| 1.5% | 1 | 2 | 1 | 16 | 2 | 2 |
| 2.0% | 15 | 3 | 2 | 11 | 5 | 4 |
| 2.5% | 12 | 4 | 4 | 3 | 7 | 10 |
| 3.0% | 7 | 7 | 6 | 2 | 6 | 12 |
| 3.5% | 3 | 3 | 14 | 2 | 3 | 15 |
| 4.0% | 0 | 3 | 17 | 0 | 0 | 20 |
| (b) 0.05% aqueous solution | | | | | | |
| 4.0% | | | | 17 | 2 | 1 |
| 4.5% | 20 | 0 | 0 | 12 | 3 | 5 |
| 5.0% | 17 | 2 | 1 | 3 | 10 | 7 |
| 5.5% | 11 | 5 | 4 | 3 | 7 | 10 |
| 6.0% | 5 | 9 | 6 | 0 | 2 | 18 |
| 6.5% | 2 | 4 | 12 | 0 | 0 | 20 |
| 7.0% | 0 | 1 | 19 | | | |

It is seen from the results given in Table 14, (a) and (b) that the sweetness of sample No. 8 as a 0.02% aqueous solution corresponds to a sugar concentration of 3% (sweetness 150 times), and as a 0.05% aqueous solution, to a sugar concentration of 6% (sweetness 120 times). On the other hand, the sweetness of sample No. 9 corresponds to a sugar concentration of 2.5% and 5%, respectively. It is judged therefore that the sweetness of the improved sweetener was slightly weaker than the sweetness corresponding to the stevioside used.

(3) Test for the quality of the taste of the improved sweetener

The improved sweetener (sample No. 9) was compared with the control (sample No. 8) in regard to the quality of sweetness in the same way as in Example 1. The results are shown in Table 15.

TABLE 15

| Sugar concentration (%) | Sample No. 8 (control) | | | Sample No. 9 (improved sweetener) | | |
|---|---|---|---|---|---|---|
| | Better | Same | Worse | Better | Same | Worse |
| | Quality of sweetness | | | | | |
| 3 | 0 | 5 | 15 | 15 | 5 | 0 |
| 6 | 0 | 2 | 18 | 18 | 2 | 0 |
| 10 | 0 | 0 | 20 | 20 | 0 | 0 |

It is clear from the results given in Table 15 that the quality of the sweetness of the improved sweetener (sample No. 9) is superior to the control (sample No. 8) at any sweetness level.

(4) Separation and determination of $\beta$-1,4-galactosyl stevioside

Figure 6:
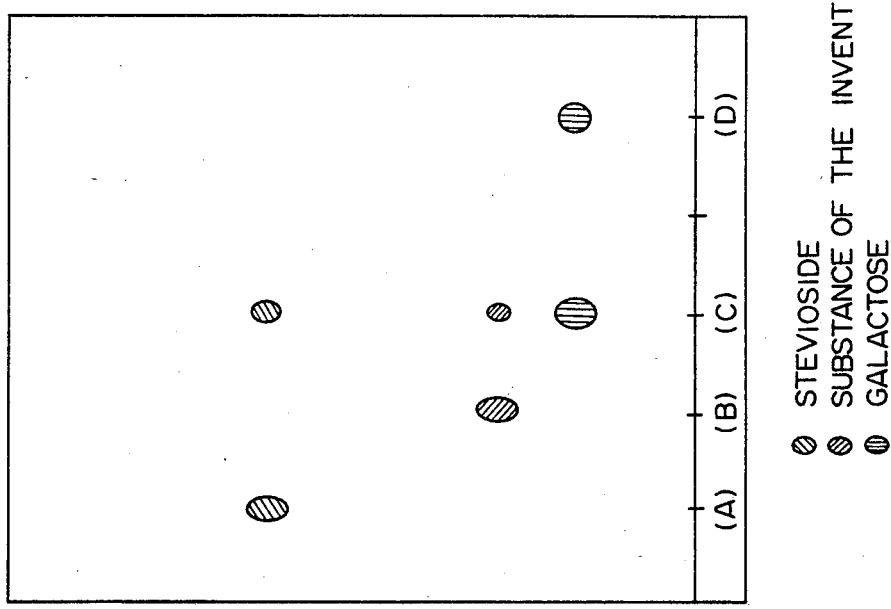
FIG. 6 is a thin-layer chromatogram, in which (A), (B), (C) and (D) respectively represent stevioside, β-1,4-galactosyl stevioside, a β-galactosidase-treated product of stevioside, and galactose.

The transfer reaction product (i.e. the improved sweetener) was purified by using an adsorbent resin and an ion-exchange resin, concentrated under reduced pressure, dried in vacuum, and dissolved in a mixed solvent composed of chloroform, methanol and water in a ratio of 30:25:4. The solution was chromatographed on a column filled with Wakogel C-200 (silica gel, Wako Pure Chemical Co., Ltd.). The column was eluted with the aforesaid solvent to separate fractions. As a result, fractions regarded as dulcoside A, stevioside, rebaudioside C and rebaudioside A were extracted in this sequence, and finally, a fraction considered to the $\beta$-1,4-glactosyl stevioside was extracted. The final fraction was concentrated under reduced pressure, and dried in vacuum to give a white powder. One milliliter of an about 2% aqueous solution of the resulting powder was taken into a test tube, and $\beta$-galactosidase (a product of Boehringer Mannheim, Germany) was added in a concentration of 6 units/ml. The reaction was carried out at 25° C. for 30 hours. After the reaction, the reaction product was spotted on a silica gel plate (60F, Merck & Co.). As a control, stevioside, the substance before treatment with $\beta$-galactosidase (the substance of this invention), and D-galactose were also spotted. The plate was developed with a developing solvent composed of chloroform, methanol and water in a ratio of 30:20:4. After full air-drying, concentrated sulfuric acid containing 0.2% of anisaldehyde was sprayed onto the plate and it was heated at 100° C. for 10 minutes to induce coloration. The resulting chromatogram is shown in FIG. 6. It is seen from FIG. 6 that in the case of the sample (C) obtained by treatment with $\beta$-galactosidase, a spot at an Rf value of 0.66 ascribed to stevioside (A) and a spot at an Rf value of 0.28 ascribed to D-galactose (D) appeared. In the case of the substance (B) of this invention used as a control, a spot was observed only at an Rf value of 0.33.

Figure 7:
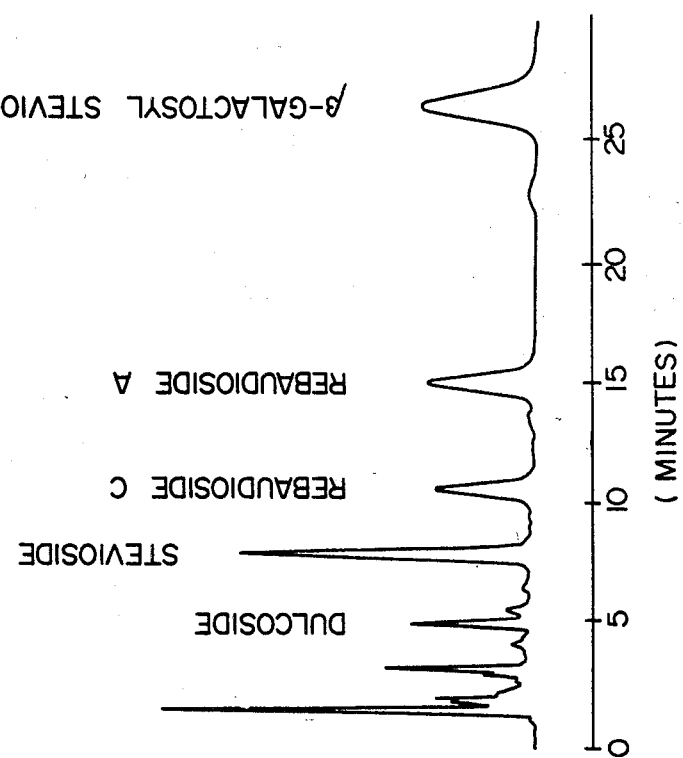
FIG. 7 shows a high-performance chromatographic chart of a β-galactosyltransferase-treated stevioside.

The reaction solution was analyzed by high-performance liquid chromatography (Model LC-3A, Shimazu Seisakusho Co. Ltd.) under the following conditions. The results are shown in FIG. 7. In addition to the peaks seen in the raw materials before the reaction (FIG. 5), the formation of a new product, $\beta$-1,4-galactosyl stevioside, was determined at r.t 26.44 minutes.

Analyzing conditions for high-performance liquid chromatography:

| | |
|---|---|
| (1) Column: | Lichrosorb-NH$_2$ 4.6 $\phi$ × 250 |
| (2) Movingphase: | CH$_3$CN:water = 78:22 (by volume) |
| (3) Flow rate: | 2 ml/min. |
| (4) Pressure: | 30 kg/cm$^2$ |
| (5) Wavelength: | 200 nm |

These results led to the determination that the substance newly formed by the reaction is a substance resulting from the $\beta$-1,4 bonding of an equimolar proportion of D-galactose to stevioside, i.e. $\beta$-1,4-monogalactosyl stevioside.

(5) Test for the sweetness of $\beta$-1,4-galactosyl stevioside

Aqueous solutions of $\beta$-1,4-galactosyl stevioside collected by column chromatography in concentrations of 0.02 and 0.05% were prepared, and the same sweetness test as in Example 1 was carried out. The results are shown in Table 16.

TABLE 16

| Sugar concentration (%) | Sample β-1,4-galactosyl stevioside Comparison of sweetness | | |
|---|---|---|---|
| | Stronger | Same | Weaker |
| (a) 0.02% aqueous solution | | | |
| 1.0 | 18 | 2 | 0 |
| 1.5 | 12 | 7 | 1 |
| 2.0 | 7 | 8 | 5 |
| 2.5 | 3 | 6 | 11 |

| Sugar concentration | Sample β-1,4-galactosyl stevioside Comparison of sweetness | | |
|---|---|---|---|
| | Stronger | Same | Weaker |
| (b) 0.05% aqueous solution | | | |
| 2.0% | 19 | 1 | 0 |
| 2.5% | 16 | 2 | 2 |
| 3.0% | 13 | 4 | 3 |
| 3.5% | 4 | 11 | 5 |
| 4.0% | 2 | 6 | 12 |

It is seen from the results of Table 16 that the sweetness of β-1,4-galactosyl stevioside as a 0.02% aqueous solution corresponds to a sugar concentration of 2% (sweetness 100 times), and as a 0.05% aqueous solution, to a sugar concentration of 3.5% (sweetness 70 times).

(6) Test for the quality of the taste of β-1,4-galactosyl stevioside.

β-1,4-Galactosyl stevioside was compared with pure stevioside (control) in regard to the quality of sweetness in the same way as in Example 1. The results are shown in Table 7.

TABLE 17

| Sugar concentration (%) | Sample | | | | | |
|---|---|---|---|---|---|---|
| | Pure stevioside | | | β-1,4-galactosyl stevioside | | |
| | Quality of sweetness | | | | | |
| | Better | Same | Worse | Better | Same | Worse |
| 3 | 0 | 2 | 18 | 18 | 2 | 0 |
| 6 | 0 | 1 | 19 | 19 | 1 | 0 |
| 10 | 0 | 0 | 20 | 20 | 0 | 0 |

It is seen from the results given in Table 17 that the quality of the sweetness of β-1,4-galactosyl stevioside is superior to stevioside at any sweetness level. According to the senses of the panelists, β-1,4-galactosyl stevioside does not have the defects of persisting unpleasant aftertastes such as bitterness and astringency, but showed mild sweetness with sharp disappearance of aftertaste, which is comparatively close to the sweetness of sugar.

EXAMPLE 14

*Rhodotorula minuta* IFO-1540 was inoculated in the same culture medium as used in Example 12, and cultivated at 30° C. for 48 hours with shaking.

The resulting cells were treated in the same way as in Example 12, and used in the same way as a source of β-galactosyl transferase. After the same transfer reaction for 135 hours, the cells were removed. The resulting reaction solution was a mixed solution containing stevioside, rebaudioside C, rebaudioside A, and β-1,4-galactosyl stevioside resulting from the β-1,4 galactosylation of about 6% of stevioside. The mixed solution was purified, concentrated, and dried in the same way as in Example 1 to give an improved sweetener which showed the same degree and quality of sweetness as in Example 13.

EXAMPLE 15

*Rhodotorula lactosa* (IFO-1424) was inoculated in the same culture medium as in Example 12 and cultivated at 30° C. for 48 hours with shaking in the same way as in Example 12. The resulting cells were treated in the same way as in Example 12 and reacted under the same conditions as in Example 12. After the reaction for 120 hours, the cells were removed. The resulting reaction solution was a mixed solution containing stevioside, rebaudioside A, rebaudioside C, and β-1,4-galactosyl stevioside resulting from the β-1,4-galactosylation of about 30% of stevioside. The mixed solution was purified and concentrated to dryness in the same way as in Example 1 to give β-1,4-galactosyl stevioside which showed the same degree and quality of sweetness as in Example 13.

EXAMPLE 16

(1) Transfer reaction

Twenty grams of purified stevioside (Stevia-DIC) and 60 g of GLYLOID 3S (a tradename for a product of Dainippon Pharmaceutical Co., Ltd.) were dissolved in 2 liters of a 0.02M potassium hydrogen phosphate buffer (pH 5.0), and 2 g of an enzyme, CELLULOSIN PC-5 (a tradename for a product of Ueda Chemical Co., Ltd.) was added. With stirring the reaction was carried out at 45° C. for 72 hours. In the same way as in Example 1-(2), an improved powdery sweetener (sample No. 11) of a stevioside derivative mainly containing a β-1,4-galactosyl linkage, and a control sample (sample No. 1) were prepared from the resulting reaction solution.

(2) Test for the sweetness of the improved sweetener

The test was carried out in the same way as in Example 1. The results are shown in Table 18.

TABLE 18

| Sugar concentration (%) | Sample | | | | | |
|---|---|---|---|---|---|---|
| | Sample No. 10 (control) | | | Sample No. 11 (improved sweetener) | | |
| | Comparison of sweetness | | | | | |
| | Stronger | Same | Weaker | Stronger | Same | Weaker |
| (a) 0.02% aqueous solution | | | | | | |
| 1.0 | 20 | 0 | 0 | 20 | 0 | 0 |
| 1.5 | 17 | 2 | 1 | 15 | 3 | 2 |
| 2.0 | 14 | 4 | 2 | 12 | 5 | 3 |
| 2.5 | 11 | 5 | 4 | 7 | 7 | 6 |
| 3.0 | 6 | 8 | 6 | 3 | 4 | 13 |
| 3.5 | 3 | 3 | 14 | 1 | 3 | 16 |
| 4.0 | 0 | 3 | 17 | 0 | 0 | 20 |
| (b) 0.05% aqueous solution | | | | | | |
| 4.0 | / | / | / | 17 | 2 | 1 |
| 4.5 | 20 | 0 | 0 | 12 | 5 | 3 |
| 5.0 | 16 | 3 | 1 | 6 | 7 | 7 |
| 5.5 | 11 | 4 | 5 | 4 | 6 | 10 |
| 6.0 | 6 | 6 | 8 | 0 | 3 | 17 |
| 6.5 | 2 | 3 | 15 | 0 | 0 | 20 |
| 7.0 | 0 | 1 | 19 | / | / | / |

It is seen from the results given in Table 18, (a) and (b) that the sweetness of sample No. 10 as a 0.02% aqueous solution corresponds to a sugar concentration of 3% (sweetness 150 times), and as a 0.05% aqueous solution, to a sugar concentration of 6% (sweetness 120 times). On the other hand, the sweetness of sample No.

11 corresponds to a sugar concentration of 2.5% and 5% respectively. It was judged therefore that the sweetness of the improved sweetener is slightly weaker than the sweetness corresponding to the stevioside used.

(3) Test for the quality of the taste of the improved sweetener

Sample No. 11 was compared with sample No. 10 (control) in regard to the quality of sweetness in the same way as in Example 1. The results are shown in Table 19.

TABLE 19

| Sugar concentration (%) | Sample No. 10 (control) Quality of sweetness | | | Sample No. 11 (improved sweetener) Quality of sweetness | | |
|---|---|---|---|---|---|---|
| | Better | Same | Worse | Better | Same | Worse |
| 3 | 0 | 4 | 16 | 16 | 4 | 0 |
| 6 | 0 | 2 | 18 | 18 | 2 | 0 |
| 10 | 0 | 0 | 20 | 20 | 0 | 0 |

The results given in Table 19 led to the determination that the quality of the sweetness of the improved sweetener (sample No. 11) is superior to the control (sample No. 10) at any sweetness level.

(4) Separation and determination of the reaction product

The transfer reaction product (i.e., the modified stevioside) was purified by using an adsorbent resin and an ion-exchange resin, concentrated under reduced pressure, dried in vacuum, and dissolved in a mixed solvent composed of chloroform, methanol and water in a ratio of 30:20:4. The solution was chromatographed on a column of Wakogel C-300 (silica gel produced by Wako Pure Chemical Co., Ltd.). The column was eluted with the aforesaid solvent to separate various fractions. As a result, fractions regarded as dulcoside A, stevioside, rebaudioside C and rebaudioside A were extracted in this sequence, and finally, a fraction considered to be a modified stevioside other than rebaudioside A was extracted. The last fraction was concentrated under reduced pressure, and dried in vacuum to give a white powder. Separately, GLYLOID 3S and CELLULOSIN PC5 were dissolved in a 0.02M potassium hydrogen phosphate buffer (pH 5.0), and with stirring, reacted at 45° C. for 72 hours. After the reaction, the reaction mixture was analyzed by gas chromatography using TMS-PZ (a tradename for a product of Tokyo Chemical Industry, Co., Ltd.). The formation of glucose, xylose and galactose as monosaccharides, and disaccharides and trisaccharides resulting from the bonding of these monosaccharides was determined.

Figure 8:
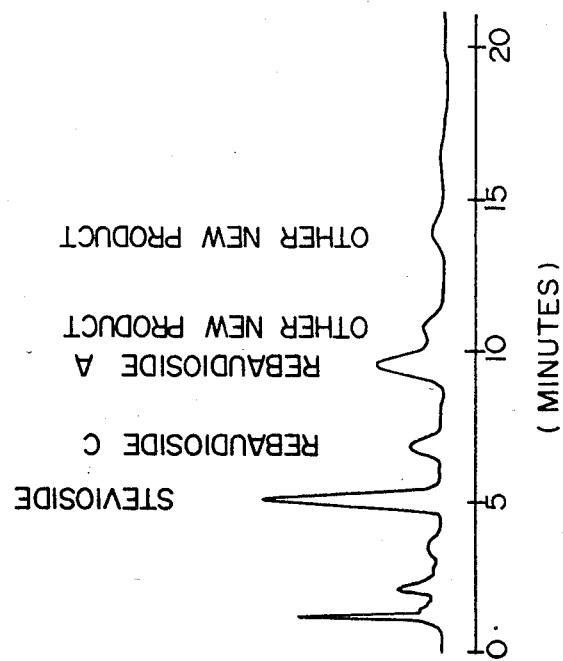
FIG. 8 shows a high-performance liquid chromatographic chart of a sugar transferase-treated product of stevioside and tamarind seed extract.

The reaction mixture was analyzed by high-performance liquid chromatography (Model LC-3A produced by Shimazu Seisakusho Co. Ltd.) under the following conditions. The results are shown in FIG. 8. In addition to the peaks seen in the starting materials before the reaction (FIG. 5), the formation of a new reaction product was observed.

Analyzing conditions for high-performance liquid chromatography

| | | |
|---|---|---|
| (1) Column: | Lichrosorb-NH$_2$, 4$\phi$ × 150 | |
| (2) Moving phase: | CH$_3$CN:water = 81:19 (by volume) | |
| (3) Flow rate: | 2 ml/min. | |
| (4) Pressure: | 30 kg/cm$^2$ | |
| (5) Wavelength: | 200 nm | |

It was judged from these results that the compound newly formed by the reaction was a single compound or a mixture resulting from the bonding of an equimolar or larger proportion of at least one of glucose, xylose, galactose and oligosaccharides of these to stevioside.

(5) Test for the sweetness of the reaction product (modified stevioside other than rebaudioside A)

Aqueous solutions of the reaction product collected by column chromatography in concentrations of 0.02% and 0.05% were prepared, and the same sweeetness test as in Example 1 was conducted. The results are shown in Table 20.

TABLE 20

| Sugar concentration (%) | Sample Reaction product Comparison of sweetness | | |
|---|---|---|---|
| | Stronger | Same | Weaker |
| (a) 0.02% aqueous solution | | | |
| 1.0 | 17 | 3 | 0 |
| 1.5 | 11 | 5 | 4 |
| 2.0 | 7 | 7 | 6 |
| 2.5 | 2 | 3 | 15 |
| (b) 0.05% aqueous solution | | | |
| 2.0 | 18 | 2 | 0 |
| 2.5 | 15 | 3 | 2 |
| 3.0 | 12 | 5 | 3 |
| 3.5 | 6 | 9 | 5 |
| 4.0 | 3 | 5 | 12 |

It was judged from the results given in Table 20 that the sweetness of the reaction product as a 0.02% aqueous solution corresponds to a sugar concentration of 2% (sweetness 100 times), and as a 0.05% aqueous solution, corresponds to a sugar concentration of 3.5% (sweetness 70 times).

(6) Test for the quality of the taste of the reaction product

The reaction product was compared with pure stevioside (control) in regard to the quality of sweetness in the same way as in Example 1. The results are shown in Table 21.

TABLE 21

| Sugar concentration (%) | Sample Pure stevioside Quality of sweetness | | | Reaction product Quality of sweetness | | |
|---|---|---|---|---|---|---|
| | Better | Same | Worse | Better | Same | Worse |
| 3 | 0 | 2 | 18 | 18 | 2 | 0 |
| 6 | 0 | 1 | 19 | 19 | 1 | 0 |
| 10 | 0 | 0 | 20 | 20 | 0 | 0 |

It is seen from the results given in Table 21 that the quality of the sweetness of the reaction product is superior to that of stevioside at any sweetness level. According to the senses of the panelists, the reaction product does not have the defect of unpleasant aftertastes such as bitterness and astringency as in stevioside, and has mild sweetness with sharp disappearance of aftertaste, which is comparatively close to sugar.

What is claimed is:

1. A process for producing a sweetener containing a β-1,3-glycosyl stevioside which is obtained by allowing an enzyme having β-1,4-glycosyl transferring activity or a microorganism capable of producing such an enzyme to react on an aqueous solution or aqueous suspension containing stevioside and at least one β-1,3-glycosyl sugar.

2. The process of claim 1 wherein the aqueous solution or suspension contains about 0.1 to 10 percent by weight of stevioside and about 0.1 to 30 percent by weight of β-1,3-glycosyl sugar.

3. The process of claim 1 wherein the aqueous solution or aqueous suspension has a pH of from about 3 to 10 and is at a temperature of from about 20° to 70° C.

4. The process of claim 1 wherein the β-1,3-glycosyl sugar is a β-1,3-glucosyl sugar.

5. The process of claim 4 wherein the β-1,3-glucosyl sugar is curdlan, pachyman, laminarin, yeast cell wall, an oligosugar compound obtained by partial hydrolysis of any one of the foregoing β-1,3-glucosyl sugars, or mixtures thereof.

6. The process of claim 1 wherein a microorganism capable of producing an enzyme having β-1,3-glucosyl transferring activity is used to react on the aqueous solution or suspension.

7. The process of claim 6 wherein said microorganism is a microorganism of the genus Streptomyces which has the property of specifically producing rebaudioside A.

8. The process of claim 7 wherein the microorganism of the genus Streptomyces is *Streptomyces* sp. DIC-108 or *Streptomyces* sp. DIC-146.

9. The process of claim 6 wherein said microorganism having β-1,3-glucosyl transferring activity is a yeast of the genus Rhodotorula.

10. The process of claim 1 wherein β-1,3-glucanase is used to react on the aqueous solution or suspension.

11. A process for producing a sweetener containing a β-1,4-glycosyl stevioside which is obtained by allowing an enzyme having β-1,4-glycosyl transferring activity or a microorganism capable of producing such an enzyme to react on an aqueous solution or aqueous suspension containing stevioside and at least one β-1,4-glycosyl sugar.

12. The process of claim 11 wherein the aqueous solution or suspension contains about 0.1 to 10 percent by weight of stevioside and about 0.1 to 30 percent by weight of β-1,4-glycosyl sugar.

13. The process of claim 11 wherein the aqueous solution or aqueous suspension has a pH of from about 3 to 10 and is at a temperature of from about 20° to 70° C.

14. The process of claim 11 wherein the β-1,4-glycosyl sugar is cellobiose or an oligosugar compound obtained by partial hydrolysis of cellulose.

15. The process of claim 11 wherein the β-1,4-glycosyl sugar is a β-1,4-galactosyl sugar.

16. The process of claim 11 wherein the β-1,4-galactosyl sugar is lactose.

17. The process of claim 11 wherein the β-1,4-glycosyl sugar is a polysaccharide obtained from tamarind seed.

18. The process of claim 11 wherein the microorganism capable of producing the enzyme having β-1,4-glycosyl transferring activity is used, said microorganism producing an enzyme having β-1,4-glucosyl transferring activity, an enzyme having β-1,4-galactosyl transferring activity, or both of said enzymes.

19. The process of claim 18 wherein the microorganism is capable of producing the enzyme having β-1,4-galactosyl transferring activity and is a yeast of the genus Rhodotorula.

20. The process of claim 11 wherein said enzyme is used and is an enzyme having β-1,4-glucosyl transferring activity, an enzyme having β-1,4-galactosyl transferring activity or a mixture of said enzymes.

* * * * *